(12) United States Patent
Lanzavecchia et al.

(10) Patent No.: US 8,298,538 B2
(45) Date of Patent: *Oct. 30, 2012

(54) HUMAN CYTOMEGALOVIRUS NEUTRALISING ANTIBODIES AND USE THEREOF

(75) Inventors: Antonio Lanzavecchia, Bellinzona (CH); Annalisa Macagno, Bellinzona (CH)

(73) Assignee: Institute for Research in Biomedicine, Bellinzona (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/087,814

(22) Filed: Apr. 15, 2011

(65) Prior Publication Data

US 2012/0076801 A1    Mar. 29, 2012

Related U.S. Application Data

(63) Continuation of application No. 12/174,568, filed on Jul. 16, 2008, now Pat. No. 7,947,274, which is a continuation-in-part of application No. 11/969,104, filed on Jan. 3, 2008, now Pat. No. 7,955,599.

(30) Foreign Application Priority Data

Jan. 4, 2007  (GB) .................................. 0700133.2

(51) Int. Cl.
 *A61K 39/42* (2006.01)
 *A61K 39/285* (2006.01)

(52) U.S. Cl. ............... 424/147.1; 424/130.1; 424/141.1; 424/159.1; 424/229.1; 424/230.1; 530/388.3; 530/388.2; 530/388.1; 530/387.1

(58) Field of Classification Search .................. None
See application file for complete search history.

(56) References Cited

U.S. PATENT DOCUMENTS

| | | | |
|---|---|---|---|
| 4,294,817 A | 10/1981 | Burgett et al. | |
| 4,313,927 A | 2/1982 | Fridlender | |
| 4,334,016 A | 6/1982 | Furukawa | |
| 4,743,562 A | 5/1988 | Rasmussen et al. | |
| 4,783,399 A | 11/1988 | Oldstone et al. | |
| 4,804,627 A | 2/1989 | Hammerling et al. | |
| 4,808,518 A | 2/1989 | Dorsett et al. | |
| 5,043,281 A | 8/1991 | Masuho et al. | |
| 5,126,130 A | 6/1992 | Lussenhop et al. | |
| 5,180,813 A | 1/1993 | Stinski | |
| 5,194,654 A | 3/1993 | Hostetler et al. | |
| 5,750,106 A | 5/1998 | Ostberg | |
| 6,120,989 A | 9/2000 | Vornhagen et al. | |
| 6,828,113 B2 | 12/2004 | Witkin | |
| 7,947,274 B2 * | 5/2011 | Lanzavecchia et al. | ... 424/147.1 |
| 7,955,599 B2 | 6/2011 | Lanzavecchia et al. | |
| 8,124,093 B2 * | 2/2012 | Lanzavecchia et al. | ... 424/147.1 |
| 2006/0216302 A1 | 9/2006 | Root-Bernstein | |
| 2008/0014208 A1 | 1/2008 | Reiter et al. | |
| 2008/0107620 A1 | 5/2008 | Khanna | |
| 2008/0187545 A1 | 8/2008 | Shenk et al. | |
| 2008/0213265 A1 | 9/2008 | Lanzavecchia et al. | |
| 2008/0248042 A1 | 10/2008 | De Re et al. | |
| 2009/0004198 A1 | 1/2009 | Nakajima et al. | |
| 2009/0162378 A1 | 6/2009 | Lai et al. | |
| 2010/0092481 A1 | 4/2010 | Lanzavecchia et al. | |
| 2012/0076801 A1 | 3/2012 | Lanzavecchia et al. | |

FOREIGN PATENT DOCUMENTS

| | | |
|---|---|---|
| EP | 122841 A1 | 10/1984 |
| EP | 128522 B1 | 12/1984 |
| EP | 162533 A2 | 11/1985 |
| EP | 165830 A1 | 12/1985 |
| EP | 198086 B1 | 10/1986 |
| EP | 248909 B1 | 12/1987 |
| EP | 277071 A2 | 8/1988 |
| EP | 0314161 A1 | 5/1989 |
| EP | 484765 A2 | 5/1992 |
| EP | 527785 B1 | 2/1993 |
| EP | 534102 B1 | 3/1993 |
| EP | 564735 B1 | 10/1993 |
| EP | 680333 B1 | 11/1995 |
| EP | 683675 A1 | 11/1995 |
| EP | 802979 B1 | 10/1997 |
| EP | 832253 B1 | 4/1998 |
| EP | 835122 A1 | 4/1998 |
| EP | 837928 B1 | 4/1998 |
| EP | 882132 B1 | 12/1998 |
| EP | 926155 A2 | 6/1999 |
| EP | 960336 B1 | 12/1999 |
| EP | 964686 A1 | 12/1999 |
| EP | 973536 A1 | 1/2000 |
| EP | 996730 A1 | 5/2000 |
| EP | 1003841 A1 | 5/2000 |
| EP | 1034289 A1 | 9/2000 |
| EP | 1061943 B1 | 12/2000 |
| EP | 1304574 B1 | 4/2003 |
| RU | 2239453 C2 | 11/2004 |
| WO | 88/03952 A2 | 6/1988 |

(Continued)

OTHER PUBLICATIONS

Adler, Barbara et al., "Role of human cytomegalovirus UL131A in cell type-specific virus entry and release," Journal of General Virology, vol. 87:2451-2460 (2006).

(Continued)

*Primary Examiner* — Benjamin P Blumel
(74) *Attorney, Agent, or Firm* — Nelson Mullins Riley & Scarborough LLP; Jane E. Remillard, Esq.; Jeanne M. DiGiorgio, Esq.

(57) ABSTRACT

The invention relates to neutralizing antibodies and antibody fragments having high potency in neutralizing hCMV, wherein said antibodies and antibody fragments are specific for a combination of hCMV proteins UL130 and UL131A, or for a combination of hCMV proteins UL128, UL130 and UL131A. The invention relates also to immortalized B cells that produce, and to epitopes that bind to, such antibodies and antibody fragments. In addition, the invention relates to the use of the antibodies, antibody fragments, and epitopes in screening methods as well as in the diagnosis and therapy of disease.

10 Claims, 7 Drawing Sheets

FOREIGN PATENT DOCUMENTS

| | | |
|---|---|---|
| WO | 90/01497 A1 | 2/1990 |
| WO | 91/04277 A1 | 4/1991 |
| WO | 91/05876 A1 | 5/1991 |
| WO | 93/21952 A1 | 11/1993 |
| WO | 94/09136 A1 | 4/1994 |
| WO | 94/16730 A1 | 8/1994 |
| WO | 9425490 A1 | 11/1994 |
| WO | 96/37211 A1 | 11/1996 |
| WO | 98/06408 A1 | 2/1998 |
| WO | 98/33510 A1 | 8/1998 |
| WO | 98/33892 A1 | 8/1998 |
| WO | 99/04010 A1 | 1/1999 |
| WO | 99/25858 A1 | 5/1999 |
| WO | 99/45952 A2 | 9/1999 |
| WO | 00/00223 A2 | 1/2000 |
| WO | 00/16061 A2 | 3/2000 |
| WO | 03/085121 A2 | 10/2003 |
| WO | 2004/076677 A2 | 9/2004 |
| WO | 2007/068758 A1 | 6/2007 |
| WO | 2007/094423 A1 | 8/2007 |
| WO | 2007/146024 A2 | 12/2007 |
| WO | 2008/071806 A1 | 6/2008 |
| WO | 2008/084410 A2 | 7/2008 |
| WO | 2008/120203 A2 | 10/2008 |
| WO | 2009/024445 A1 | 2/2009 |
| WO | 2009/085383 A1 | 7/2009 |
| WO | 2010/007463 A1 | 1/2010 |

OTHER PUBLICATIONS

Baba, Timothy W. et al., "Human neutralizing monoclonal antibodies of the IgG1 subtype protect against mucosal simian-human immunodeficiency virus infection," Nature Medicine, vol. 6(2):200-206 (2000).
Borucki, M. et al., "A phase II, double-masked, randomized, placebo-controlled evaluation of a human monoclonal anti-Cytomegalovirus antibody (MSL-109) in combination with standard therapy versus standard therapy alone in the treatment of AIDS patients with Cytomegalovirus retinitis," Antiviral Research, vol. 64:103-111 (2004).
Clackson, Tim et al., "Making antibody fragments using phage display libraries," Nature, vol. 352:624-628 (1991).
Drosten, Christian et al., "Identification of a Novel Coronavirus in Patients with Severe Acute Respiratory Syndrome," The New England Journal of Medicine, vol. 348:1967-1976 (2003).
Foung, Steven K.H. et al., "Human Monoclonal Antibodies to Human Cytomegalovirus," The Journal of Infectious Diseases, vol. 159 (3):436-443 (1989).
Funaro, Ada et al., "Generation of potent neutralizing human monoclonal antibodies against cytomegalovirus infection from immune B cells," BMC Biotechnologies, vol. 8:85 doi:10.1186/1472-6750-8-85 (2008).
Gerna, G. et al., "Dendritic-cell infection by human cytomegalovirus is restricted to strains carrying functional UL131-128 genes and mediates efficient viral antigen presentation to CD8+ T Cells," J. Gen. Virology, vol. 86:275-284 (2005).
Gerna, Giuseppe et al., "Human cytomegalovirus serum neutralizing antibodies block virus infection of endothelial/epithelial cells, but not fibroblasts, early during primary infection," Journal of General Virology, vol. 89:853-865 (2008).
Gerna, G. et al., "Lack of transmission to polymorphonuclear leukocytes and human umbilical vein endothelial cells are as a marker of attenuation of human cytomegalovirus," J. Med. Virology, vol. 66:335-339 (2002).
Goldsby, Richard A. et al., Immunology, Fifth Edition, W.H. Freeman and Company, New York, pp. 83-85 (2003).
Hahn, G. et al., "Human cytomegalovirus UL-131-1289, genes are indispensible for virus growth in endothelial cells and virus tansfer to leukocytes," J. Virology, vol. 78(18):10023-10033 (2004).
Invitrogen, "Mammalian Cell Culture," retrieved online at: http://www.invitrogen.com/site/us/en/home/Products-and-Services/Applications/Cell-Culture.html (2010).
Lanzavecchia, Antonio, "Monoclonal antibody production by EBV transformation of B cells," not yet published U.S. Appl. No. 11/719,835, filed Feb. 26, 2004; Institute for Research in Biomedicine.
Macagno, Annalisa et al., "Isolation of Human Monoclonal Antibodies That Potently Neutralize Human Cytomegalovirus Infection by Targeting Different Epitopes on the gH/gL/UL128-131A Complex," Journal of Virology, vol. 84(2):1008-1013 (2010).
Mach, M. et al., "Complex Formation by Human Cytomegalovirus Glycoproteins M (gpUL100) and N (glUL73)," Journal of Virology, vol. 74(24):11881-11892 (2000).
Masuho, Y. et al., "Human monclonal antibodies neutralizing human cytomegalovirus," Journal of General Virology, vol. 68:1457-1461 (1987).
Mazeron, M.C. et al., "Monoclonal antibody E-13 (M-810) to human cytomegalovirus recognizes an epitope encoded by exon 2 of the major immediate early gene," Journal of General Virology, vol. 73:2699-2703 (1992).
McLean, G. et al., "Recognition of human cytomegalovirus by human primary immunoglobulins identifies an innate foundation to an adaptive immune response", J. Immunol., vol. 174:4768-4778 (2005).
Mulder, A. et al., "A human monoclonal antibody, produced following in vitro immunization, recognizing an epitope shared by HLA-A2 subtypes and HLA-A28," Tissue Antigens, vol. 42:27-34 (1993).
National BioResource Project (NBRP)::E.coli Strain, "About Cloning Vector Collection," retreived online at: http://www.shigen.nig.ac.jp/ecoli/strain/cvector/cvectorExplanation.jsp (2009).
Niedbala, Wanda G. et al., "A Comparison of Three Methods for Production of Human Hybridomas Secreting Autoantibodies," Hybridoma, vol. 17(3):299-304 (1998).
Nigro, G. et al., "Passive immunization during pregnancy for congenital cytomegalovirus infection," New England J. Medicine, vol. 353:1350-1362 (2005).
Ohlin, Mats et al., "Cytomegalovirus Glycoprotein B-Specific Antibody Analysis Using Electrochemiluminescence Detection-Based Techniques," Clinical and Diagnostic Laboratory Immunology, vol. 4(1):107-111 (1997).
Ohlin, Mats et al., "Fine Specificity of the Human Immune Response to the Major Neutralization Epitopes Expressed on Cytomegalovirus gp58/116 (gB), as Determined with Human Monoclonal Antibodies," Journal of Virology, vol. 67(2):703-710 (1993).
Patrone, M. et al., "Human cytomegalovirus UL130 protein promotes endothelial cell infection through a producer cell modification of the virion," J. Virology, vol. 79:8361-8373 (2005).
Plachter et al., "Cell types involved in replication and distribution of human cytomegalovirus," Adv Virus Res, vol. 46:195-261 (1996).
Portolano, Stefano et al., "Lack of Promiscuity in Autoantigen-Specific H and L Chain Combinations as Revealed by Human H and L Chain 'Roulette'," The Journal of Immunology, vol. 150(3):880-887 (1993).
Rudikoff, Stuart et al., "Single amino acid substitution altering antigen-binding specificity," Proc. Natl. Acad. Sci. USA, vol. 79:1979-1983 (1982).
Ryckman, Brent J. et al., "Characterization of the Human Cytomegalovirus gH/gL/UL128-131 Complex That Mediates Entry into Epithelial and Endothelial Cells," Journal of Virology, vol. 82(1):60-70 (2008).
Takekoshi, M. M et al., "Human monoclonal anti-HCMV neutralizing antibody from phage display libraries," Journal of Virological Methods, vol. 74:89-98 (1998).
Vajdos, Felix F. et al., "Comprehensive Functional Maps of the Antigen-binding Site of an Anti-ErbB2 Antibody Obtained with Shotgun Scanning Mutagenesis," J. Mol. Biol., vol. 320:415-428 (2002).
Wang, Dai et al., "Human Cytomegalovirus UL131 Open Reading Frame Is Required for Epithelial Cell Tropism," Journal of Virology, vol. 79(16):10330-10338 (2005).
Wang, Dai et al., "Human cytomegalovirus virion protein complex required for epithelial and endothelial cell tropism," PNAS, vol. 102(50):18153-18158 (2005).
European Office Action for Application No. 08737590, dated Feb. 17, 2010.
International Preliminary Report on Patentability for Application No. PCT/IB2008/001111, dated Jul. 7, 2009.
International Preliminary Report on Patentability for Application No. PCT/IB2009/006641, dated Jan. 18, 2011.

International Search Report for Application No. PCT/IB2008/001111, dated Nov. 3, 2008.
International Search Report for Application No. PCT/IB2008/002683, dated Mar. 30, 2009.
International Search Report for Application No. PCT/IB2009/006641, dated Jun. 24, 2010.
Invitation to Pay Additional Fees with Partial International Search for Application No. PCT/IB2008/006641, dated Mar. 11, 2010.
Written Opinion for Application No. PCT/IB2008/002683, dated Jul. 7, 2009.

Andreoni, K.A. et al., "Human CMV/IGIV (CytoGam) neutralizes human cytomegalovirus (HCMV) infectivity and prevents intracellular signal transduction after HCMV exposure," Transplant Infectious Disease, vol. 3(s2):25-30 (2001).
Eurasian Office Action for Application No. 201170204/26, 3 pages, dated Feb. 15, 2011.
European Office Action for Application No. 08875708.3, 11 pages, dated Apr. 12, 2012.

* cited by examiner

Figure 3

1F11-VH caggaacaactggtggagtctggggggaggcgtggtccagcctgggaggtccgtgagactctcctgtgtggcctctgg
attcaccttcagttcctatgctatgcactgggtccgccaggctccgggcaaggggctggaatgggtgtcacttatat
cctttgatggagacaataaatactatgcagactccgtgaggggccgattcaccatctccagagacagttccagaag
acgctctttctgcaaatgaacagcctgagagctgaggacacggctatatattactgtgcgagagaggagttagtcgg
attgatgcctccctactacaattatggtttggacgtctggggccaaggaccacggtcaccgtctcctcag QRQLVESGGDVVQPGRSVRLSCVASGFTFSSYAMHWVRQAPGKGLEWVSLISFDGDNKYYADSVRGRFTISRDSSQK
TLFLQMNSLRVEDTAIYYCAREELVGLMPPYYNYGLDVWGQGTTVTVSS

1F11-VL cagtctgtgttgacgcagccgccctcagtgtctgcggccccaggacagaaggtcaccatctcctgctctggaagcag
ctccaacattggaaataaattttgtatcctggtaccagcaactcccgggaacagcccccaaactcctcatttatgaca
atgataggcgaccctcagggattcctgaccgattctctggctccaagtctgacacgtcagccaccctggtcatcacc
ggactccagactggggacgaggccgattactactgcgaaacatgggatggcagcctgaatcctgctgtggtattcgg
cggagggaccaggctgaccgtcctag QSVLTQPPSVSAAPGQKVTISCSGSSSNIGNNFVSWYQQLPGTAPKLLIYDNDRRPSGIPDRFSGSKSDTSATLVIT
GLQTGDEADYYCETWDGSLNPAVVFGGGTRLTVL

2F4-VH caggtgctgctggtggagtctgggggaggcgtggtccagcctggaggtccctgagactctcctgtgcagcgtctgg
attcagttttcaatacatgggatgcactgggtccgccaggctccaggcaaggggctggagtgggtggcagttatat
gggatgatggaagtaaaatgtaccatgcggactccgtgaagggccgattcaccatctccagagacaattccaaaac
acactgtatctgcaaatgaacagtctgagagccgaggatacggctgtgtattactgtgcgagagacgagggtgcaat
aatgctgcacgccatgactgactacggttggacgtctggggccaaggaccacagtcaccgtctcctcag QVLLVESGGGVVQPGRSLRLSCAASGFSFNTYGMHWVRQAPGKGLEWVAVIWDDGSKMYHADSVKGRFTISRDNSKN
TLYLQMNSLRAEDTAVYYCARDEGAIMLHAMTDYGLDVWGQGTTVTVSS

2F4-VL tcctatgagctgaatcagccacccctcagtgtccgtgtcccaggacagacagccaccatcacctgctctggagataa
tttgggggatgagtttgcttgctggtatcagcagaagccaggccagtccctgtgctggtcatctatcaggattcca
gcgggcctcagggatccctgagcgattctctggctccagctctgggaacacagccactctgaccatccgcgggacc
caggctatggatgaggctgactactactgtcaggcgtgggacagcagcactgcccattatgtcttcggaactgggac
caaggtcaccgtcctag SYELNQPPSVSVSPGQTATITCSGDNLGDEFACWYQQKPGQSPVLVIYQDSKRPSGIPERFSGSSSGNTATLTIRGT
QAMDEADYYCQAWDSSTAHYVFGTGTKVTVL

Figure 5

SA2 - VH caggtgcagctggtgcagtctggggctgaggtgaggaagcctgggtcctcggtgaaggtctcctgca
aggcttctggaggcaccttcagcagctatgttatccactgggtgcgacaggcccctggacaagggct
tgagtggatggggggatcatccctatctttaatacagcaaactacgcacagaaggtccagggcaga
gtcacgattaccgcggacgaatccacgagcacagcctacatggagctgagcagcctgagatctgaag
acactgccatatattactgtgcgagggattttctatcaggtcctatggaaatgcccggcggctacta
cggtttggacgtctggggccaagggaccacggtcaccgtctcctca QVQLVQSGAEVRKPGSSVKVSCKASGGTFSSYVIHWVRQAPGQGLEWMGGIIPIFNTANYAQKVQGR
VTITADESTSTAYMELSSLRSEDTAIYYCARDFLSGPMEMPGGYYGLDVWGQGTTVTVSS

SA2 - VK gacatcgtgatgacccagtctccagactccctggctgtgtctctgggcgagagggccaccatcaact
gcaagtccagccagagtgttttatacagttccaacaataagaactacttagcttggtaccagcagaa
accaggacagcctcctaagctgctcatttactgggcatctacccgggaatccggggtccctgaccga
ttcagtggcagcgggtctgggacagatttcactctcaccatcagcagcctgcaggctgaagatgtgg
cagtttattactgtcagcaatatatagtactcctatcacttcggccaagggacacgactggagat
taaa DIVMTQSPDSLAVSLGERATINCKSSQSVLYSSNNKNYLAWYQQKPGQPPKLLIYWASTRESGVPDR
FSGSGSGTDFTLTISSLQAEDVAVYYCQQYYSTPITFGQGTRLEIK

Figure 7

6G4-VH gaggtgcagctggtgcagtctggagcagaggtgaaaaagcccgggaagtctctgaggatctcctgtaaggcttctgg
atacaggtttaccagctactacatgccatgggtgcgccacatgcccgggaaaggcctggagtggatgggaatcatct
atcctggtgactctgatatcacatacagcccgtccttccaaggccaggtcaccatctcagccgacaagtccgccact
accgcctacctgcaatggagcagcctgagggcctcggacaccgccatgtactactgtgcgagactctcattaacaga
gtccggtgactacgtcggtgcgtttgatatctggggccaagggacaatggtcaccgtctcttcag EVQLVQSGAEVKKPGKSLRISCKASGYRFTSYYIAWVRHMPGKLEWMGIIYPGDSDITYSPSFQGQVTISADKSAT
TAYLQWSSLRASDTAMYYCARLSLTRSGDYVGAFDIWGQGTMVTVSS

6G4 - VK gattttgtgctgactcagtctccactctccctgcccgtcacccttggacagccggcctccatctcctgcaggtctaa
tcaaagcctcgtatacagtgatgacaacatcttcttgaattggttccagcaggggccaggccaacctccaaggcgcc
taatttataaggtttctaacccgggactctggggtcccagacagattcagcggcagtgggtcaggcactgatttcaca
ctgaaaatcagcagggtggaggctgaggatgttggcgtttattactgcatgcaaggtagaactggcctcctctatt
cacttcggccctgggaccaaagtggatatcaaac DFVLTQSPLSLAVTLGQPASISCRSSQSLVYSDDNIFLNWFQQGPGQPPRRLIYKVSNRDSVPDRFSGSGSGTDFT
LKISRVEABDVGVYYCMQGRTWPLYTFGPGTKVDIK

SEQUENCE LISTING

<160> NUMBER OF SEQ ID NOS: 66

<210> SEQ ID NO 1
<211> LENGTH: 8
<212> TYPE: PRT
<213> ORGANISM: Homo sapiens

<400> SEQUENCE: 1

Gly Phe Thr Phe Ser Ser Tyr Ala
1               5

<210> SEQ ID NO 2
<211> LENGTH: 8
<212> TYPE: PRT
<213> ORGANISM: Homo sapiens

<400> SEQUENCE: 2

Ile Ser Phe Asp Gly Asp Asn Lys
1               5

<210> SEQ ID NO 3
<211> LENGTH: 19
<212> TYPE: PRT
<213> ORGANISM: Homo sapiens

<400> SEQUENCE: 3

Ala Arg Glu Glu Leu Val Gly Leu Met Pro Pro Tyr Tyr Asn Tyr Gly
1               5                   10                  15

Leu Asp Val

<210> SEQ ID NO 4
<211> LENGTH: 8
<212> TYPE: PRT
<213> ORGANISM: Homo sapiens

<400> SEQUENCE: 4

Ser Ser Asn Ile Gly Asn Asn Phe
1               5

<210> SEQ ID NO 5
<211> LENGTH: 3
<212> TYPE: PRT
<213> ORGANISM: Homo sapiens

<400> SEQUENCE: 5

Asp Asn Asp
1

<210> SEQ ID NO 6
<211> LENGTH: 12
<212> TYPE: PRT
<213> ORGANISM: Homo sapiens

<400> SEQUENCE: 6

Glu Thr Trp Asp Gly Ser Leu Asn Pro Ala Val Val
1               5                   10

<210> SEQ ID NO 7
<211> LENGTH: 126
<212> TYPE: PRT
<213> ORGANISM: Homo sapiens

<400> SEQUENCE: 7

Gln Glu Gln Leu Val Glu Ser Gly Gly Val Val Gln Pro Gly Arg
1               5                   10                  15

Ser Val Arg Leu Ser Cys Val Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Leu Ile Ser Phe Asp Gly Asp Asn Lys Tyr Tyr Ala Asp Ser Val
    50                  55                  60

Arg Gly Arg Phe Thr Ile Ser Arg Asp Ser Ser Gln Lys Thr Leu Phe
65                  70                  75                  80

Leu Gln Met Asn Ser Leu Arg Val Glu Asp Thr Ala Ile Tyr Tyr Cys
                85                  90                  95

Ala Arg Glu Glu Leu Val Gly Leu Met Pro Pro Tyr Tyr Asn Tyr Gly
            100                 105                 110

Leu Asp Val Trp Gly Gln Gly Thr Thr Val Thr Val Ser Ser
        115                 120                 125

<210> SEQ ID NO 8
<211> LENGTH: 111
<212> TYPE: PRT
<213> ORGANISM: Homo sapiens

<400> SEQUENCE: 8

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Phe Val Ser Trp Tyr Gln Gln Leu Pro Gly Thr Ala Pro Lys Leu Leu
             35                  40                  45

Ile Tyr Asp Asn Asp Arg Arg Pro Ser Gly Ile Pro Asp Arg Phe Ser
 50                  55                  60

Gly Ser Lys Ser Asp Thr Ser Ala Thr Leu Val Ile Thr Gly Leu Gln
 65                  70                  75                  80

Thr Gly Asp Glu Ala Asp Tyr Tyr Cys Glu Thr Trp Asp Gly Ser Leu
                 85                  90                  95

Asn Pro Ala Val Val Phe Gly Gly Gly Thr Arg Leu Thr Val Leu
             100                 105                 110

<210> SEQ ID NO 9
<211> LENGTH: 379
<212> TYPE: DNA
<213> ORGANISM: Homo sapiens

<400> SEQUENCE: 9
caggaacaac tggtggagtc tgggggaggc gtggtccagc ctgggaggtc cgtgagactc      60
tcctgtgtgg cctctggatt caccttcagt tcctatgcta tgcactgggt ccgccaggct     120
ccgggcaagg ggctggaatg ggtgtcactt atatcctttg atggagacaa taaatactat     180
gcagactccg tgaggggccg attcacaatc tccagagaca gttcccagaa gacgctcttt     240
ctgcaaatga acagcctgag agttgaggac acggctatat attactgtgc gagagaggag     300
ttagtcggat tgatgcctcc ctactacaat tatggtttgg acgtctgggg ccaagggacc     360
acggtcaccg tctcctcag                                                  379

<210> SEQ ID NO 10
<211> LENGTH: 334
<212> TYPE: DNA
<213> ORGANISM: Homo sapiens

<400> SEQUENCE: 10
cagtctgtgt tgacgcagcc gccctcagtg tctgcggccc caggacagaa ggtcaccatc      60
tcctgctctg gaagcagctc caacattgga aataattttg tatcctggta ccagcaactc     120
cccggaacag cccccaaact cctcatttat gacaatgata ggcgaccctc agggattcct     180
gaccgattct ctggctccaa gtctgacacg tcagccaccc tggtcatcac cggactccag     240
actggggacg aggccgatta ctactgcgaa acatgggatg gcagcctgaa tcctgctgtg     300
gtattcggcg gagggaccag gctgaccgtc ctag                                 334

<210> SEQ ID NO 11
<211> LENGTH: 8
<212> TYPE: PRT
<213> ORGANISM: Homo sapiens

<400> SEQUENCE: 11

Gly Phe Ser Phe Asn Thr Tyr Gly
 1               5

<210> SEQ ID NO 12
<211> LENGTH: 8
<212> TYPE: PRT
<213> ORGANISM: Homo sapiens

<400> SEQUENCE: 12

Ile Trp Asp Asp Gly Ser Lys Met
 1               5

<210> SEQ ID NO 13
<211> LENGTH: 19
<212> TYPE: PRT
<213> ORGANISM: Homo sapiens

<400> SEQUENCE: 13

```
Ala Arg Asp Glu Gly Ala Ile Met Leu His Ala Met Thr Asp Tyr Gly
1               5                   10                  15

Leu Asp Val
```

<210> SEQ ID NO 14
<211> LENGTH: 6
<212> TYPE: PRT
<213> ORGANISM: Homo sapiens

<400> SEQUENCE: 14

```
Asn Leu Gly Asp Glu Phe
1               5
```

<210> SEQ ID NO 15
<211> LENGTH: 3
<212> TYPE: PRT
<213> ORGANISM: Homo sapiens

<400> SEQUENCE: 15

```
Gln Asp Ser
1
```

<210> SEQ ID NO 16
<211> LENGTH: 11
<212> TYPE: PRT
<213> ORGANISM: Homo sapiens

<400> SEQUENCE: 16

```
Gln Ala Trp Asp Ser Ser Thr Ala His Tyr Val
1               5                   10
```

<210> SEQ ID NO 17
<211> LENGTH: 126
<212> TYPE: PRT
<213> ORGANISM: Homo sapiens

<400> SEQUENCE: 17

```
Gln Val Leu Leu Ala Glu Ser Gly Gly Gly Val Val Gln Pro Gly Arg
1               5                   10                  15

Ser Leu Arg Leu Ser Cys Ala Ala Ser Gly Phe Ser Phe Asn Thr Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Lys Met Tyr His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Glu Gly Ala Ile Met Leu His Ala Met Thr Asp Tyr Gly
            100                 105                 110

Leu Asp Val Trp Gly Gln Gly Thr Thr Val Thr Val Ser Ser
        115                 120                 125
```

<210> SEQ ID NO 18

```
<211> LENGTH: 108
<212> TYPE: PRT
<213> ORGANISM: Homo sapiens

<400> SEQUENCE: 18

Ser Tyr Ala Leu Asn Gln Pro Pro Ser Val Ser Val Ser Pro Gly Gln
1               5                   10                  15

Thr Ala Thr Ile Thr Cys Ser Gly Asp Asn Leu Gly Asp Glu Phe Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Ser Ser Gly Asn Thr Ala Thr Leu Thr Ile Arg Gly Thr Gln Ala Met
65                  70                  75                  80

Asp Glu Ala Asp Tyr Tyr Cys Gln Ala Trp Asp Ser Ser Thr Ala His
                85                  90                  95

Tyr Val Phe Gly Thr Gly Thr Lys Val Thr Val Leu
            100                 105

<210> SEQ ID NO 19
<211> LENGTH: 379
<212> TYPE: DNA
<213> ORGANISM: Homo sapiens

<400> SEQUENCE: 19
caggtgctgc tggcggagtc tgggggaggc gtggtccagc ctgggaggtc cctgagactc      60
tcctgtgcag cgtctggatt cagtttcaat acatatggga tgcactgggt ccgccaggct     120
ccaggcaagg ggctggagtg gtggcagtt atatgggatg atggaagtaa aatgtaccat      180
gcggactccg tgaagggccg attcaccatc tccagagaca attccaaaaa cacactgtat     240
ctccaaatga acagtctgag agccgaggat acggctgtgt attactgtgc gagagacgag     300
ggtgcaataa tgctgcacgc catgactgac tacggtttgg acgtctgggg ccaagggacc     360
acagtcaccg tctcctcag                                                  379

<210> SEQ ID NO 20
<211> LENGTH: 325
<212> TYPE: DNA
<213> ORGANISM: Homo sapiens

<400> SEQUENCE: 20
tcctatgcgc tgaatcagcc accctcagtg tccgtgtccc caggacagac agccaccatc      60
acctgctctg gagataattt gggggatgag tttgcttgct ggtatcagca gaagccaggc     120
cagtctcctg tgctggtcat ctatcaggat tccaagcggc cctcagggat ccctgagcga     180
ttctctggct ccagctctgg gaacacagcc actctgacca tccgcgggac ccaggctatg     240
gatgaggctg actactactg tcaggcgtgg gacagcagca ctgcccatta tgtcttcgga     300
actgggacca aggtcaccgt cctag                                            325

<210> SEQ ID NO 21
<211> LENGTH: 24
<212> TYPE: DNA
<213> ORGANISM: Homo sapiens

<400> SEQUENCE: 21
ggattcacct tcagttccta tgct                                             24
```

-continued

```
<210> SEQ ID NO 22
<211> LENGTH: 24
<212> TYPE: DNA
<213> ORGANISM: Homo sapiens

<400> SEQUENCE: 22
atatcctttg atggagacaa taaa                                            24

<210> SEQ ID NO 23
<211> LENGTH: 57
<212> TYPE: DNA
<213> ORGANISM: Homo sapiens

<400> SEQUENCE: 23
gcgagagagg agttagtcgg attgatgcct ccctactaca attatggttt ggacgtc        57

<210> SEQ ID NO 24
<211> LENGTH: 24
<212> TYPE: DNA
<213> ORGANISM: Homo sapiens

<400> SEQUENCE: 24
agctccaaca ttggaaataa tttt                                            24

<210> SEQ ID NO 25
<211> LENGTH: 9
<212> TYPE: DNA
<213> ORGANISM: Homo sapiens

<400> SEQUENCE: 25 gacaatgat                                                              9

<210> SEQ ID NO 26
<211> LENGTH: 36
<212> TYPE: DNA
<213> ORGANISM: Homo sapiens

<400> SEQUENCE: 26
gaaacatggg atggcagcct gaatcctgct gtggta                               36

<210> SEQ ID NO 27
<211> LENGTH: 24
<212> TYPE: DNA
<213> ORGANISM: Homo sapiens

<400> SEQUENCE: 27
ggattcagtt tcaatacata tggg                                            24

<210> SEQ ID NO 28
<211> LENGTH: 24
<212> TYPE: DNA
<213> ORGANISM: Homo sapiens

<400> SEQUENCE: 28
atatgggatg atggaagtaa aatg                                            24

<210> SEQ ID NO 29
<211> LENGTH: 57
<212> TYPE: DNA
<213> ORGANISM: Homo sapiens

<400> SEQUENCE: 29
gcgagagacg agggtgcaat aatgctgcac gccatgactg actacggttt ggacgtc        57
```

```
<210> SEQ ID NO 30
<211> LENGTH: 18
<212> TYPE: DNA
<213> ORGANISM: Homo sapiens

<400> SEQUENCE: 30
aatttggggg atgagttt                                                    18

<210> SEQ ID NO 31
<211> LENGTH: 9
<212> TYPE: DNA
<213> ORGANISM: Homo sapiens

<400> SEQUENCE: 31 caggattcc                                                               9

<210> SEQ ID NO 32
<211> LENGTH: 33
<212> TYPE: DNA
<213> ORGANISM: Homo sapiens

<400> SEQUENCE: 32
caggcgtggg acagcagcac tgcccattat gtc                                   33

<210> SEQ ID NO 33
<211> LENGTH: 8
<212> TYPE: PRT
<213> ORGANISM: Homo sapiens

<400> SEQUENCE: 33

Gly Gly Thr Phe Ser Ser Tyr Val
1               5

<210> SEQ ID NO 34
<211> LENGTH: 8
<212> TYPE: PRT
<213> ORGANISM: Homo sapiens

<400> SEQUENCE: 34

Ile Ile Pro Ile Phe Asn Thr Ala
1               5

<210> SEQ ID NO 35
<211> LENGTH: 20
<212> TYPE: PRT
<213> ORGANISM: Homo sapiens

<400> SEQUENCE: 35

Ala Arg Asp Phe Leu Ser Gly Pro Met Glu Met Pro Gly Gly Tyr Tyr
1               5                   10                  15

Gly Leu Asp Val
            20

<210> SEQ ID NO 36
<211> LENGTH: 12
<212> TYPE: PRT
<213> ORGANISM: Homo sapiens

<400> SEQUENCE: 36

Gln Ser Val Leu Tyr Ser Ser Asn Asn Lys Asn Tyr
1               5                   10

<210> SEQ ID NO 37
<211> LENGTH: 3
<212> TYPE: PRT
```

<213> ORGANISM: Homo sapiens

<400> SEQUENCE: 37

Trp Ala Ser
1

<210> SEQ ID NO 38
<211> LENGTH: 9
<212> TYPE: PRT
<213> ORGANISM: Homo sapiens

<400> SEQUENCE: 38

Gln Gln Tyr Tyr Ser Thr Pro Ile Thr
1               5

<210> SEQ ID NO 39
<211> LENGTH: 127
<212> TYPE: PRT
<213> ORGANISM: Homo sapiens

<400> SEQUENCE: 39

Gln Val Gln Leu Val Gln Ser Gly Ala Glu Val Arg Lys Pro Gly Ser
1               5                   10                  15

Ser Val Lys Val Ser Cys Lys Ala Ser Gly Gly Thr Phe Ser Ser Tyr
                20                  25                  30

Val Ile His Trp Val Arg Gln Ala Pro Gly Gln Gly Leu Glu Trp Met
            35                  40                  45

Gly Gly Ile Ile Pro Ile Phe Asn Thr Ala Asn Tyr Ala Gln Lys Val
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Ile Tyr Tyr Cys
                85                  90                  95

Ala Arg Asp Phe Leu Ser Gly Pro Met Glu Met Pro Gly Gly Tyr Tyr
                100                 105                 110

Gly Leu Asp Val Trp Gly Gln Gly Thr Thr Val Thr Val Ser Ser
            115                 120                 125

<210> SEQ ID NO 40
<211> LENGTH: 113
<212> TYPE: PRT
<213> ORGANISM: Homo sapiens

<400> SEQUENCE: 40

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Ile Thr Phe Gly Gln Gly Thr Arg Leu Glu Ile
                100                 105                 110

Lys

<210> SEQ ID NO 41
<211> LENGTH: 382
<212> TYPE: DNA
<213> ORGANISM: Homo sapiens

<400> SEQUENCE: 41

| | | | | | |
|---|---|---|---|---|---|
| caggtgcagc | tggtgcagtc | tggggctgag | gtgaggaagc | ctgggtcctc | ggtgaaggtc | 60 |
| tcctgcaagg | cttctggagg | caccttcagc | agctatgtta | tccactgggt | gcgacaggcc | 120 |
| cctggacaag | ggcttgagtg | gatgggggg | atcatcccta | tctttaatac | agcaaactac | 180 |
| gcacagaagg | tccagggcag | agtcacgatt | accgcggacg | aatccacgag | cacagcctac | 240 |
| atggagctga | gcagcctgag | atctgaagac | actgccatat | attactgtgc | gagggatttt | 300 |
| ctatcaggtc | ctatggaaat | gcccggcggc | tactacggtt | tggacgtctg | gggccaaggg | 360 |
| accacggtca | ccgtctcctc | ag | | | | 382 |

<210> SEQ ID NO 42
<211> LENGTH: 340
<212> TYPE: DNA
<213> ORGANISM: Homo sapiens

<400> SEQUENCE: 42

| | | | | | |
|---|---|---|---|---|---|
| gacatcgtga | tgacccagtc | tccagactcc | ctggctgtgt | ctctgggcga | gagggccacc | 60 |
| atcaactgca | agtccagcca | gagtgtttta | tacagttcca | acaataagaa | ctacttagct | 120 |
| tggtaccagc | agaaaccagg | acagcctcct | aagctgctca | tttactgggc | atctacccgg | 180 |
| gaatccgggg | tccctgaccg | attcagtggc | agcgggtctg | ggacagattt | cactctcacc | 240 |
| atcagcagcc | tgcaggctga | agatgtggca | gtttattact | gtcagcaata | ttatagtact | 300 |
| cctatcacct | tcggccaagg | gacacgactg | gagattaaac | | | 340 |

<210> SEQ ID NO 43
<211> LENGTH: 24
<212> TYPE: DNA
<213> ORGANISM: Homo sapiens

<400> SEQUENCE: 43
ggaggcacct tcagcagcta tgtt                                                24

<210> SEQ ID NO 44
<211> LENGTH: 24
<212> TYPE: DNA
<213> ORGANISM: Homo sapiens

<400> SEQUENCE: 44
atcatcccta tctttaatac agca                                                24

<210> SEQ ID NO 45
<211> LENGTH: 60
<212> TYPE: DNA
<213> ORGANISM: Homo sapiens

<400> SEQUENCE: 45
gcgagggatt ttctatcagg tcctatggaa atgcccggcg gctactacgg tttggacgtc         60

<210> SEQ ID NO 46
<211> LENGTH: 36
<212> TYPE: DNA
<213> ORGANISM: Homo sapiens

<400> SEQUENCE: 46

```
cagagtgttt tatacagttc aacaataag aactac                                  36

<210> SEQ ID NO 47
<211> LENGTH: 9
<212> TYPE: DNA
<213> ORGANISM: Homo sapiens

<400> SEQUENCE: 47 tgggcatct                                                                9

<210> SEQ ID NO 48
<211> LENGTH: 27
<212> TYPE: DNA
<213> ORGANISM: Homo sapiens

<400> SEQUENCE: 48
cagcaatatt atagtactcc tatcacc                                           27

<210> SEQ ID NO 49
<211> LENGTH: 126
<212> TYPE: PRT
<213> ORGANISM: Homo sapiens

<400> SEQUENCE: 49

Gln Val Gln Leu Val Glu Ser Gly Gly Val Val Gln Pro Gly Arg
1               5                   10                  15

Ser Leu Arg Leu Ser Cys Ala Ala Ser Gly Phe Ser Phe Asn Thr Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Lys Met Tyr His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Glu Gly Ala Ile Met Leu His Ala Met Thr Asp Tyr Gly
            100                 105                 110

Leu Asp Val Trp Gly Gln Gly Thr Thr Val Thr Val Ser Ser
        115                 120                 125

<210> SEQ ID NO 50
<211> LENGTH: 378
<212> TYPE: DNA
<213> ORGANISM: Homo sapiens

<400> SEQUENCE: 50
caggtgcagc tggtggagtc tgggggaggc gtggtccagc ctgggaggtc cctgagactc        60
tcctgtgcag cgtctggatt cagtttcaat acatatggga tgcactgggt ccgccaggct       120
ccaggcaagg ggctggagtg gtggcagtt atatggatg atggaagtaa aatgtaccat        180
gcggactccg tgaagggccg attcaccatc tccagagaca attccaaaaa cacactgtat       240
ctccaaatga acagtctgag agccgaggat acggctgtgt attactgtgc gagagacgag       300
ggtgcaataa tgctgcacgc catgactgac tacggtttgg acgtctgggg ccaagggacc       360
acagtcaccg tctcctca                                                    378

<210> SEQ ID NO 51
<211> LENGTH: 8
```

```
<212> TYPE: PRT
<213> ORGANISM: Homo sapiens

<400> SEQUENCE: 51

Gly Tyr Arg Phe Thr Ser Tyr Tyr
1               5

<210> SEQ ID NO 52
<211> LENGTH: 8
<212> TYPE: PRT
<213> ORGANISM: Homo sapiens

<400> SEQUENCE: 52

Ile Tyr Pro Gly Asp Ser Asp Ile
1               5

<210> SEQ ID NO 53
<211> LENGTH: 17
<212> TYPE: PRT
<213> ORGANISM: Homo sapiens

<400> SEQUENCE: 53

Ala Arg Leu Ser Leu Thr Glu Ser Gly Asp Tyr Val Gly Ala Phe Asp
1               5                   10                  15

Ile

<210> SEQ ID NO 54
<211> LENGTH: 11
<212> TYPE: PRT
<213> ORGANISM: Homo sapiens

<400> SEQUENCE: 54

Gln Ser Leu Val Tyr Ser Asp Asp Asn Ile Phe
1               5                   10

<210> SEQ ID NO 55
<211> LENGTH: 3
<212> TYPE: PRT
<213> ORGANISM: Homo sapiens

<400> SEQUENCE: 55

Lys Val Ser
1

<210> SEQ ID NO 56
<211> LENGTH: 11
<212> TYPE: PRT
<213> ORGANISM: Homo sapiens

<400> SEQUENCE: 56

Met Gln Gly Arg His Trp Pro Pro Leu Phe Thr
1               5                   10

<210> SEQ ID NO 57
<211> LENGTH: 24
<212> TYPE: DNA
<213> ORGANISM: Homo sapiens

<400> SEQUENCE: 57
ggatacaggt ttaccagcta ctac                                        24

<210> SEQ ID NO 58
<211> LENGTH: 24
<212> TYPE: DNA
<213> ORGANISM: Homo sapiens
```

<400> SEQUENCE: 58
atctatcctg gtgactctga tatc                                          24

<210> SEQ ID NO 59
<211> LENGTH: 51
<212> TYPE: DNA
<213> ORGANISM: Homo sapiens

<400> SEQUENCE: 59
gcgagactct cattaacaga gtccggtgac tacgtcggtg cgtttgatat c             51

<210> SEQ ID NO 60
<211> LENGTH: 33
<212> TYPE: DNA
<213> ORGANISM: Homo sapiens

<400> SEQUENCE: 60
caaagcctcg tatacagtga tgacaacatc ttc                                33

<210> SEQ ID NO 61
<211> LENGTH: 9
<212> TYPE: DNA
<213> ORGANISM: Homo sapiens

<400> SEQUENCE: 61 aaggtttct                                                           9

<210> SEQ ID NO 62
<211> LENGTH: 33
<212> TYPE: DNA
<213> ORGANISM: Homo sapiens

<400> SEQUENCE: 62
atgcaaggta gacactggcc tcctctattc act                                33

<210> SEQ ID NO 63
<211> LENGTH: 124
<212> TYPE: PRT
<213> ORGANISM: Homo sapiens

<400> SEQUENCE: 63

Glu Val Gln Leu Val Gln Ser Gly Ala Glu Val Lys Lys Pro Gly Lys
1               5                   10                  15

Ser Leu Arg Ile Ser Cys Lys Ala Ser Gly Tyr Arg Phe Thr Ser Tyr
            20                  25                  30

Tyr Ile Ala Trp Val Arg His Met Pro Gly Lys Gly Leu Glu Trp Met
        35                  40                  45

Gly Ile Ile Tyr Pro Gly Asp Ser Asp Ile Thr Tyr Ser Pro Ser Phe
    50                  55                  60

Gln Gly Gln Val Thr Ile Ser Ala Asp Lys Ser Ala Thr Ala Tyr
65                  70                  75                  80

Leu Gln Trp Ser Ser Leu Arg Ala Ser Asp Thr Ala Met Tyr Tyr Cys
                85                  90                  95

Ala Arg Leu Ser Leu Thr Glu Ser Gly Asp Tyr Val Gly Ala Phe Asp
            100                 105                 110

Ile Trp Gly Gln Gly Thr Met Val Thr Val Ser Ser
        115                 120

<210> SEQ ID NO 64
<211> LENGTH: 114

```
<212> TYPE: PRT
<213> ORGANISM: Homo sapiens

<400> SEQUENCE: 64

Asp Phe Val Leu Thr Gln Ser Pro Leu Ser Leu Ala Val Thr Leu Gly
1               5                   10                  15

Gln Pro Ala Ser Ile Ser Cys Arg Ser Asn Gln Ser Leu Val Tyr Ser
            20                  25                  30

Asp Asp Asn Ile Phe Leu Asn Trp Phe Gln Gln Gly Pro Gly Gln Pro
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Met Gln Gly
                85                  90                  95

Arg His Trp Pro Pro Leu Phe Thr Phe Gly Pro Gly Thr Lys Val Asp
            100                 105                 110

Ile Lys

<210> SEQ ID NO 65
<211> LENGTH: 373
<212> TYPE: DNA
<213> ORGANISM: Homo sapiens

<400> SEQUENCE: 65
gaggtgcagc tggtgcagtc tggagcagag gtgaaaaagc ccggggaagtc tctgaggatc      60 tcctgtaagg cttctggata caggtttacc agctactaca tcgcctgggt gcgccacatg     120
cccgggaaag gcctggagtg gatggggatc atctatcctg gtgactctga tatcacatac     180
agcccgtcct tccaaggcca ggtcaccatc tcagccgaca gtccgccac taccgcctac      240 ctgcaatgga gcagcctgag gcctcggac accgccatgt actactgtgc gagactctca      300
ttaacagagt ccggtgacta cgtcggtgcg tttgatatct ggggccaagg gacaatggtc      360
accgtctctt cag                                                         373

<210> SEQ ID NO 66
<211> LENGTH: 343
<212> TYPE: DNA
<213> ORGANISM: Homo sapiens

<400> SEQUENCE: 66
gattttgtgc tgactcagtc tccactctcc ctggccgtca cccttggaca gccggcctcc      60
atctcctgca ggtctaatca aagcctcgta tacagtgatg acaacatctt cttgaattgg     120
tttcagcagg ggccaggcca acctccaagg cgcctaattt ataaggtttc taaccgggac     180
tctggggtcc cagacagatt cagcggcagt gggtcaggca ctgatttcac actgaaaatc     240
agcagggtgg aggctgagga tgttggcgtt tattactgca tgcaaggtag acactggcct     300
cctctattca ctttcggccc tgggaccaaa gtggatatca aac                        343
```

HUMAN CYTOMEGALOVIRUS NEUTRALISING ANTIBODIES AND USE THEREOF

This application is a Continuation of U.S. patent application Ser. No. 12/174,568 filed Jul. 16, 2008, which is a continuation in part of U.S. patent application Ser. No. 11/969,104, filed Jan. 3, 2008, which claims priority to British Patent Application No. GB 0700133.2, filed Jan. 4, 2007. The entire contents of each of these patents and patent applications, along with all documents cited therein, are hereby incorporated herein by reference.

BACKGROUND

This invention relates to potent, neutralizing antibodies having specificity for human cytomegalovirus, and immortalized B cells that produce such monoclonal antibodies. The invention also relates to the epitopes that the antibodies bind to as well as the use of the antibodies and the epitopes in screening methods as well as the diagnosis, prophylaxis and therapy of disease.

Human cytomegalovirus (hCMV) is a widely distributed pathogen that may cause severe pathology in immunosuppressed adults and upon infection of the fetus and has been implicated in chronic diseases such as atherosclerosis. hCMV infects multiple cell types including fibroblasts, endothelial, epithelial and hematopoietic cells [1]. In vitro propagated attenuated strains of hCMV, which are being developed as candidate vaccines, have lost the tropism for endothelial cells, while retaining the capacity to infect fibroblasts [2]. Two viral glycoprotein complexes are believed to control the cellular tropism of hCMV. A complex of gH, gL and gO is required for infection of fibroblasts, while a complex of gH, gL and proteins encoded by the UL131-UL128 genes are responsible for infection of endothelial cells, epithelial cells and dendritic cells [2-8].

Hyperimmune globulins are already commercialized for the prophylaxis of hCMV disease associated with transplantation and recent evidence indicates that they have therapeutic effect in pregnant women [9]. This therapeutic approach is limited by the low amount of neutralizing antibody that can be transferred and for this reason the availability of human antibodies (such as human monoclonal antibodies) with high neutralizing capacity would be highly desirable. However the target of hCMV neutralizing antibodies remains to be established. Although some antibodies to gH, gB and UL128 and UL130 gene products have demonstrated in vitro neutralizing activities [7, 10, 11] and an antibody to gH has been evaluated in clinical trials which were discontinued due to lack of therapeutic effects, the neutralizing potency of the monoclonal antibodies isolated so far is modest, since neutralization was observed at antibody concentrations ranging from 0.5 to 20 microgram/ml. Further, the current methods typically measure the neutralising potency of anti-hCMV antibodies using fibroblasts as target cells. However, hCMV is also known to cause pathology by infecting other cell types such as endothelial, epithelial cells and leukocytes. Known antibodies to UL128 and UL130 show very low potency in neutralising infection of endothelial cells [7] and there do not appear to be any monoclonal antibodies available that would be capable of neutralising infection of non-fibroblast target cells with high potency.

There is therefore a need for the production of neutralizing antibodies against hCMV infection of non-fibroblast cells as well as the elucidation of the target to which such antibodies bind.

SUMMARY OF INVENTION

The invention is based, in part, on the discovery of novel antibodies that neutralize hCMV with high potency as well as novel epitopes to which the antibodies of the invention bind. Accordingly, in one embodiment, the invention comprises a neutralizing antibody and antibody fragments having high potency in neutralizing hCMV, wherein said antibody and antibody fragments are specific for a combination of hCMV proteins UL130 and UL131A, or for a combination of hCMV proteins UL128, UL130 and UL131A.

In another embodiment the invention comprises a nucleic acid molecule encoding an antibody or an antibody fragment of the invention.

In yet another embodiment the invention comprises a vector comprising a nucleic acid molecule encoding an antibody or an antibody fragment of the invention.

In a further embodiment the invention comprises a cell comprising a vector comprising a nucleic acid molecule of the invention.

In another embodiment the invention comprises an immortalized B cell clone expressing an antibody of the invention.

In yet another embodiment the invention comprises an epitope which binds to an antibody of the invention.

In a further embodiment the invention comprises an immunogenic polypeptide comprising an epitope which binds to an antibody of the invention.

In another embodiment the invention comprises a ligand which binds to an epitope which binds to an antibody of the invention.

In a further embodiment the invention comprises a method for producing antibodies having high potency in neutralizing hCMV, wherein said antibody is specific for a combination of the hCMV proteins UL128, UL130 and UL131A or for a combination of the hCMV proteins UL130 and UL131A. The method comprises culturing an immortalized B cell clone expressing an antibody of the invention and isolating antibodies from the B cell.

In another embodiment the invention comprises a pharmaceutical composition comprising an antibody or antibody fragment, a nucleic acid of the invention, an immortalized B cell clone expressing an antibody of the invention, or an immunogenic polypeptide comprising an epitope which binds to an antibody of the invention.

In a further embodiment the invention comprises an antibody or antibody fragment having high potency in neutralizing hCMV, wherein said antibody or antibody fragment is specific for a combination of the hCMV proteins UL130 and UL131A or for a combination of the hCMV proteins UL128, UL130, UL131A, a nucleic acid encoding an antibody or an antibody fragment as above, an immortalized B cell clone expressing an antibody having high potency in neutralizing hCMV wherein said antibody is specific for a combination of the hCMV proteins UL130 and UL131A or for a combination of the hCMV proteins UL128, UL130 and UL131A, or an immunogenic polypeptide comprising an epitope which binds to an antibody or antibody fragment having high potency in neutralizing hCMV, wherein said antibody is specific for a combination of the hCMV proteins UL130 and UL131A or for a combination of the hCMV proteins UL128, UL130 and UL131A for use in therapy or diagnosis.

In another embodiment the invention comprises a kit for the diagnosis of hCMV infection comprising antibodies or antibody fragments of the invention, or a nucleic acid encoding an antibody or an antibody fragment of the invention.

In another embodiment the invention comprises a method for preparing a recombinant cell. The method comprises sequencing nucleic acid from an immortalized B cell clone expressing an antibody of the invention and using the sequence information to prepare nucleic acid for inserting into an expression host in order to permit expression of the antibody of interest in that host.

In a further embodiment the invention comprises a method for producing antibodies having high potency in neutralizing hCMV and specific for a combination of the hCMV proteins UL128, UL130 and UL131A or for a combination of the hCMV proteins UL130 and UL131A. The method comprises culturing or sub-culturing an expression host obtainable by the method described above and, optionally, purifying the antibody of interest.

In another embodiment the invention comprises a method of screening for polypeptides that can induce an immune response against hCMV, comprising screening polypeptide libraries using an antibody or an antibody fragment of the invention.

BRIEF DESCRIPTION OF DRAWINGS

FIG. 3 shows the nucleotide and amino acid sequences of the variable regions of the heavy and light chains of antibodies 1F11 (SEQ ID NOs: 9 and 10 and SEQ ID NOs: 7 and 8, respectively) and 2F4 (SEQ ID NOs: 19 and 20 and SEQ ID NOs: 17 and 18, respectively). The CDR sequences are in bold.

FIG. 5 shows the nucleotide and amino acid sequences of the variable regions of the heavy and light chains of antibody 5A2 (SEQ ID NOs:41 and 42 and SEQ ID NOs: 39 and 40, respectively). The CDR sequences are in bold.

FIG. 7 shows the nucleotide and amino acid sequences of the variable regions of the heavy and light chains of antibody 6G4 (SEQ ID NOs: 65 and 66 and SEQ ID NOs: 63 and 64, respectively). The CDR sequences are in bold.

DETAILED DESCRIPTION OF THE INVENTION

Figure 1:
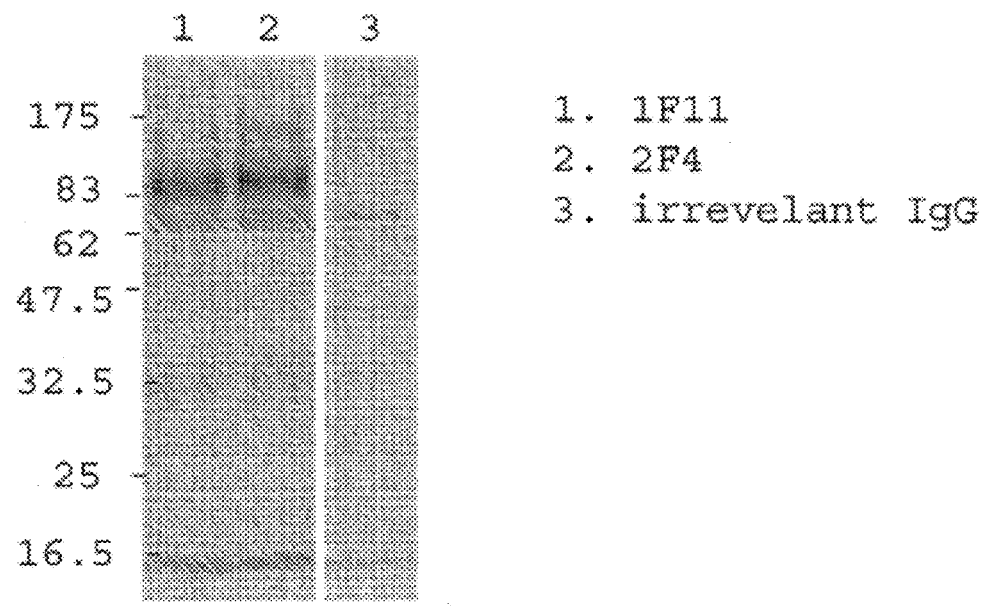
FIG. 1 shows a SDS-PAGE which demonstrates that human monoclonal antibodies (1) 1F11 and (2) 2F4 precipitate complexes of hCMV proteins, whereas irrelevant IgG does not.

The invention is based on the production of antibodies and antibody fragments that neutralize hCMV infection and which have a particularly high potency in neutralizing hCMV infection. Such antibodies are desirable, as only low concentrations are required in order to neutralize a given amount of virus. This facilitates higher levels of protection whilst administering lower amounts of antibody. Human monoclonal antibodies and the immortalized B cell clones that secrete such antibodies are also included within the scope of the invention.

The inventors have discovered that antibodies directed to a combination of UL130 and UL131A are particularly effective in neutralizing hCMV. The combination may be a complex of UL130 and UL131A forming an epitope recognized by the antibody or an antibody may be directed to one of UL130 and UL131A, the presence of the other protein being necessary for specificity. In addition, the inventors have discovered that antibodies directed to a combination of UL128, UL130 and UL131A are particularly effective in neutralizing hCMV. Without being bound to any theory, this combination may be a precise complex of UL128, UL130 and UL131A forming a unique epitope recognized by the antibody.

The invention also relates to the characterization of the epitope to which the antibodies bind and the use of that epitope in raising an immune response.

The invention also relates to various methods and uses involving the antibodies of the invention and the epitopes to which they bind.

Antibodies

The invention provides monoclonal or recombinant antibodies having particularly high potency in neutralizing hCMV. The invention also provides fragments of these recombinant or monoclonal antibodies, particularly fragments that retain the antigen-binding activity of the antibodies, for example which retain at least one complementarity determining region (CDR) specific for a combination of hCMV proteins UL130 and UL131A or retain at least one CDR specific for a combination of the hCMV proteins UL128, UL130 and UL131A.

In this specification, by "high potency in neutralizing hCMV" is meant that an antibody molecule of the invention neutralizes hCMV in a standard assay at a concentration much lower than antibodies known in the art, for example compared to MSL-109, 8F9 or 3E3. For example, the term "high potency" is used to refer to an antibody or an antibody fragment of the invention that has $IC_{50}$ of less than about 2 µg/ml, (i.e. the concentration of antibody required for 50% neutralization of a clinical isolate of hCMV is about 2 µg/ml or less).

In one embodiment, the antibody or antibody fragment of the present invention can neutralise hCMV at a concentration of 1 µg/ml or less (i.e. 0.95, 0.9, 0.85, 0.8, 0.75, 0.7, 0.6, 0.5, 0.4, 0.3, 0.2, 0.1, 0.05, 0.01 µg/ml or lower). In another embodiment, the antibody or antibody fragment of the present invention can neutralise hCMV at a concentration of 0.16 µg/ml or lower (i.e. 0.15, 0.125, 0.1, 0.075, 0.05, 0.025, 0.02, 0.015, 0.0125, 0.01, 0.0075, 0.005, 0.004, 0.003, 0.002 µg/ml or lower). In another embodiment, the antibody can neutralise hCMV at a concentration of 0.016 µg/ml or lower (i.e. at 0.015, 0.013, 0.01, 0.008, 0.005, 0.003, 0.001, 0.0005 µg/ml or lower). This means that only very low concentrations of antibody are required for 50% neutralisation of a clinical isolate of hCMV in vitro compared to the concentration of known antibodies, e.g., MSL-109, required for neutralisation of the same titre of hCMV. Potency can be measured using a standard neutralisation assay as known to one of skill in the art.

The antibodies of the invention are able to neutralize hCMV infection of several kinds of cells. Preferably, an antibody according to the invention prevents infection of fibroblasts or endothelial cells. More preferably, an antibody according to the invention prevents infection of endothelial cells. Preferably, an antibody according to the invention prevents infection of both fibroblasts and endothelial cells. The antibodies of the invention preferably also prevent infection of epithelial cells, retinal cells and dendritic cells.

These antibodies can be used as prophylactic or therapeutic agents upon appropriate formulation, or as a diagnostic tool.

A "neutralizing antibody" is one that can neutralize the ability of that pathogen to initiate and/or perpetuate an infection in a host. The invention provides a neutralizing human monoclonal antibody, wherein the antibody recognizes an antigen from hCMV.

Preferably, an antibody according to the invention has specificity for a combination of the hCMV proteins UL130 and UL131A.

Preferably an antibody according to the invention is a monoclonal antibody referred to herein as 1F11 or 2F4. These antibodies were initially isolated from a hCMV infected donor, and are produced by the immortalized B cell clones referred to as 1F11 or 2F4. These antibodies have been shown to neutralize hCMV infection of endothelial cells, epithelial cells, retinal cells and dendritic cells. In addition, the antibodies 5A2 and 9A11, isolated from a different hCMV infected donor, show the same specificity for a combination of UL130 and UL131A and the ability to neutralize hCMV infection of endothelial cells, epithelial cells, retinal cells and dendritic cells. These antibodies are produced by the immortalized B cell clones referred to as 5A2 and 9A11, respectively.

1F11 consists of a heavy chain having the amino acid sequence recited in SEQ ID NO:7 and a light chain having the amino acid sequence recited in SEQ ID NO:8. 2F4 consists of a heavy chain having the amino acid sequence recited in SEQ ID NO:17 and a light chain having the amino acid sequence recited in SEQ ID NO:18. The CDRs of the antibody heavy chains are referred to as CDRH1, CDRH2 and CDRH3, respectively. Similarly, the CDRs of the antibody light chains are referred to as CDRL1, CDRL2 and CDRL3, respectively. The position of the CDR amino acids are defined according to the IMGT numbering system [12, 13, 14] as: CDR1-IMGT positions 27 to 38, CDR2-IMGT positions 56 to 65 and CDR3-IMGT positions 105 to 117.

5A2 consists of a heavy chain having the amino acid sequence recited in SEQ ID NO:39 and a light chain having the amino acid sequence recited in SEQ ID NO:40.

The amino acid sequences of the CDRs of these antibodies are shown in Table 1.

for CDRH2 and SEQ ID NO:13 for CDRH3. A further preferred antibody according to the invention comprises a heavy chain comprising SEQ ID NO:33 for CDRH1, SEQ ID NO:34 for CDRH2 and SEQ ID NO:35 for CDRH3.

The invention also includes an antibody comprising a light chain comprising one or more (i.e. one, two or all three) light chain CDRs from 1F11 or 2F4 (SEQ ID NOs:4-6 or 14-16). Also included is an antibody comprising a light chain comprising one or more (i.e. one, two or all three) light chain CDRs from 5A2 (SEQ ID NOs:36-38).

Preferably an antibody according to the invention comprises a light chain comprising (i) SEQ ID NO:4 for CDRL1, SEQ ID NO:5 for CDRL2 and SEQ ID NO:6 for CDRL3, or (ii) SEQ ID NO:14 for CDRL1, SEQ ID NO:15 for CDRL2 and SEQ ID NO:16 for CDRL3. A further preferred antibody according to the invention comprises a light chain comprising SEQ ID NO:36 for CDRL1, SEQ ID NO:37 for CDRL2 and SEQ ID NO:38 for CDRL3.

Preferably an antibody according to the invention comprises a heavy chain having the sequence recited in SEQ ID NO:7, 17 or 39. Preferably an antibody according to the invention comprises a light chain having the sequence recited in SEQ ID NO:8, 18 or 40.

Hybrid antibody molecules may also exist that comprise one or more CDRs from 1F11 and one or more CDRs from 2F4. Preferably, such hybrid antibodies comprise three CDRs from 1F11 and three CDRs from 2F4. Thus, preferred hybrid antibodies comprise i) the three light chain CDRs from 1F11 and the three heavy chain CDRs from 2F4, or ii) the three heavy chain CDRs from 1F11 and the three light chain CDRs from 2F4. In an alternative, such hybrids may contain one or more CDRs from 5A2.

The invention also includes nucleic acid sequences encoding part or all of the light and heavy chains and CDRs of the present invention. Preferred nucleic acid sequences according to the invention include SEQ ID NO:9 (encoding the 1F11 heavy chain variable region), SEQ ID NO:10 (encoding the

TABLE 1

|       | 1F11 | 2F4 | 5A2 |
|-------|------|-----|-----|
| CDRH1 | GFTFSSYA (SEQ ID NO: 1) | GFSFNTYG (SEQ ID NO: 11) | GGTFSSYV (SEQ ID NO: 33) |
| CDRH2 | ISFDGDNK (SEQ ID NO: 2) | IWDDGSKM (SEQ ID NO: 12) | IIPIFNTA (SEQ ID NO: 34) |
| CDRH3 | AREELVGLMPPYYNYGLDV (SEQ ID NO: 3) | ARDEGAIMLHAMTDYGLDV (SEQ ID NO: 13) | ARDFLSGPMEMPGGYYGLDV (SEQ ID NO: 35) |
| CDRL1 | SSNIGNNF (SEQ ID NO: 4) | NLGDEF (SEQ ID NO: 14) | QSVLYSSNNKNY (SEQ ID NO: 36) |
| CDRL2 | DND (SEQ ID NO: 5) | QDS (SEQ ID NO: 15) | WAS (SEQ ID NO: 37) |
| CDRL3 | ETWDGSLNPAVV (SEQ ID NO: 6) | QAWDSSTAHYV (SEQ ID NO: 16) | QQYYSTPIT (SEQ ID NO: 38) |

The invention also includes an antibody comprising a heavy chain comprising one or more (i.e. one, two or all three) heavy chain CDRs from 1F11 or 2F4 (SEQ ID NOs:1-3 or 11-13). Also included is an antibody comprising a heavy chain comprising one or more (i.e. one, two or all three) heavy chain CDRs from 5A2 (SEQ ID NOs:33-35).

Preferably an antibody according to the invention comprises a heavy chain comprising (i) SEQ ID NO:1 for CDRH1, SEQ ID NO:2 for CDRH2 and SEQ ID NO:3 for CDRH3, or (ii) SEQ ID NO:11 for CDRH1, SEQ ID NO:12

1F11 light chain variable region), SEQ ID NO:19 (encoding the 2F4 heavy chain variable region), and SEQ ID NO:20 (encoding the 2F4 light chain variable region). Preferred nucleic acid sequences encoding the various CDRs include SEQ ID NO:21 (encoding 1F11 CDRH1), SEQ ID NO:22 (encoding 1F11 CDRH2), SEQ ID NO:23 (encoding 1F11 CDRH3), SEQ ID NO:24 (encoding 1F11 CDRL1), SEQ ID NO:25 (encoding 1F11 CDRL2), SEQ ID NO:26 (encoding 1F11 CDRL3), SEQ ID NO:27 (encoding 2F4 CDRH1), SEQ ID NO:28 (encoding 2F4 CDRH2), SEQ ID NO:29 (encoding 2F4 CDRH3), SEQ ID NO:30 (encoding 2F4 CDRL1), SEQ ID NO:31 (encoding 2F4 CDRL2) and SEQ ID NO:32 (encoding 2F4 CDRL3). Further preferred nucleic acid sequences according to the invention include SEQ ID NO:41 (encoding the 5A2 heavy chain variable region), SEQ ID NO:42 (encoding the 5A2 light chain variable region), SEQ ID NO:43 (encoding 5A2 CDRH1), SEQ ID NO:44 (encoding 5A2 CDRH2), SEQ ID NO:45 (encoding 5A2 CDRH3), SEQ ID NO:46 (encoding 5A2 CDRL1), SEQ ID NO:47 (encoding 5A2 CDRL2), SEQ ID NO:48 (encoding 5A2 CDRL3). Due to the redundancy of the genetic code, variants of these sequences will exist that encode the same amino acid sequences.

In another embodiment, an antibody according to the invention has specificity for a combination of UL128, UL130 and UL131A. An antibody according to the invention is a monoclonal antibody referred to herein as 6G4. This antibody, isolated from a hCMV infected donor, is produced by the immortalized B cell clone referred to as 6G4. This antibody neutralizes hCMV infection of endothelial cells, epithelial cells, retinal cells and dendritic cells.

The heavy chain of 6G4 has the amino acid sequence recited in SEQ ID NO:63 and the light chain has the amino acid sequence recited in SEQ ID NO:64. The CDRs of the antibody heavy chains are referred to as CDRH1, CDRH2 and CDRH3, respectively. Similarly, the CDRs of the antibody light chains are referred to as CDRL1, CDRL2 and CDRL3, respectively. The amino acid sequences of the CDRs of this antibody are shown in Table 2.

TABLE 2

| 6G4 | |
|---|---|
| CDRH1 | GYRFTSYY (SEQ ID NO: 51) |
| CDRH2 | IYPGDSDI (SEQ ID NO: 52) |
| CDRH3 | ARLSLTESGDYVGAFDI (SEQ ID NO: 53) |
| CDRL1 | QSLVYSDDNIF (SEQ ID NO: 54) |
| CDRL2 | KVS (SEQ ID NO: 55) |
| CDRL3 | MQGRHWPPLFT (SEQ ID NO: 56) |

The invention also includes an antibody comprising a heavy chain comprising one or more (i.e. one, two or all three) heavy chain CDRs from 6G4 (SEQ ID NOs:51-53) or a light chain comprising one or more (i.e., one, two or all three) light chain CDRs from 6G4 (SEQ ID NOs:54-56).

In one embodiment an antibody according to the invention comprises a heavy chain comprising (i) SEQ ID NO:51 for CDRH1, SEQ ID NO:52 for CDRH2 and SEQ ID NO:53 for CDRH3.

In another embodiment the invention includes an antibody comprising a light chain comprising one or more (i.e. one, two or all three) light chain CDRs from 6G4 (SEQ ID NOs: 54-56).

In another embodiment the invention includes an antibody comprising a light chain comprising (i) SEQ ID NO:54 for CDRL1, SEQ ID NO:55 for CDRL2 and SEQ ID NO:56 for CDRL3.

In a further embodiment an antibody according to the invention has specificity for a combination of UL128, UL130 and UL131A and comprises a heavy chain having an amino acid sequence that is at least 70%, at least 75%, at least 80%, at least 85%, at least 90%, at least 95%, at least 98%, or at least 99% identical to the amino acid sequence of SEQ ID NO:63 and possessing hCMV neutralizing activity. In one embodiment, an antibody according to the invention comprises a heavy chain having the sequence recited in SEQ ID NO:63 and possessing hCMV neutralizing activity.

In another embodiment, an antibody according to the invention has specificity for a combination of UL128, UL130 and UL131A and comprises a light chain having an amino acid sequence that is at least 70%, at least 75%, at least 80%, at least 85%, at least 90%, at least 95%, at least 98%, or at least 99% identical to the amino acid sequence of SEQ ID NO:64 and possessing hCMV neutralizing activity. In yet another embodiment an antibody according to the invention comprises a light chain having the sequence recited in SEQ ID NO:64 and possessing hCMV neutralizing activity.

Antibodies of the invention also include hybrid antibody molecules that comprise one or more CDRs from 6G4 and one or more CDRs from another antibody to the same epitope. In one embodiment, such hybrid antibodies comprise three CDRs from 6G4 and three CDRs from another antibody to the same epitope. Thus, preferred hybrid antibodies comprise i) the three light chain CDRs from 6G4 and the three heavy chain CDRs from another antibody to the same epitope, or ii) the three heavy chain CDRs from 6G4 and the three light chain CDRs from another antibody to the same epitope.

In another aspect, the invention also includes nucleic acid sequences encoding part or all of the heavy and light chains and CDRs of the antibodies of the present invention. In one embodiment, nucleic acid sequences according to the invention include nucleic acid sequences having at least 70%, at least 75%, at least 80%, at least 85%, at least 90%, at least 95%, at least 98%, or at least 99% identity to the nucleic acid sequence of SEQ ID NO:65 or SEQ ID NO:66. In another embodiment, a nucleic acid sequence of the invention has the sequence of SEQ ID NO:65 (encoding the 6G4 heavy chain variable region) or SEQ ID NO:66 (encoding the 6G4 light chain variable region). In further embodiments, nucleic acid sequences of the invention include those encoding the various CDRs include SEQ ID NO:57 (encoding 6G4 CDRH1), SEQ ID NO:58 (encoding 6G4 CDRH2), SEQ ID NO:59 (encoding 6G4 CDRH3), SEQ ID NO:60 (encoding 6G4 CDRL1), SEQ ID NO:61 (encoding 6G4 CDRL2) and SEQ ID NO:62 (encoding 6G4 CDRL3).

Variant antibodies are also included within the scope of the invention. Thus, variants of the sequences recited in the application are also included within the scope of the invention. Without being bound to any theory, such variants may arise due to the degeneracy of the genetic code, as mentioned above. Alternatively, natural variants may be produced due to errors in transcription or translation or be generated by somatic mutation in vivo during the immune response or in vitro upon culturing of immortalized B cells. A variant of 2F4 is also disclosed herein. This variant comprises an additional two serine residues at the C-terminal end of the 2F4 heavy chain amino acid sequence (SEQ ID NO:17). Thus, this variant of 2F4 consists of a heavy chain having the amino acid sequence recited in SEQ ID NO:49 and a light chain having the amino acid sequence recited in SEQ ID NO:18. The nucleic acid sequence encoding the variant heavy chain is recited in SEQ ID NO:50. Thus, antibodies comprising the 2F4 variant heavy chain (SEQ ID NO:49) are included within the scope of the invention.

Further variants of the antibody sequences having improved affinity may be obtained using methods known in the art and are included within the scope of the invention. For example, amino acid substitutions may be used to obtain antibodies with further improved affinity. Alternatively, codon optimization of the nucleotide sequence may be used to improve the efficiency of translation in expression systems for the production of the antibody. Further, polynucleotides comprising a sequence optimized for antibody specificity or neutralizing activity by the application of a directed evolution method to any of the nucleic acid sequences of the invention are also within the scope of the invention.

Preferably, variant antibody sequences will share 70% or more (i.e. 80%, 85%, 90%, 95%, 97%, 98%, 99% or more) sequence identity with the sequences recited in the application. Preferably such sequence identity is calculated with regard to the full length of the reference sequence (i.e. the sequence recited in the application). Preferably, percentage identity, as referred to herein, is as determined using BLAST version 2.1.3 using the default parameters specified by the NCBI (the National Center for Biotechnology Information; http://www.ncbi.nlm.nih.gov/) [Blosum 62 matrix; gap open penalty=11 and gap extension penalty=1].

Further included within the scope of the invention are vectors, for example expression vectors, comprising a nucleic acid sequence according to the invention. Cells transformed with such vectors are also included within the scope of the invention. Examples of such cells include but are not limited to, eukaryotic cells, e.g. yeast cells, animal cells or plant cells. In one embodiment the cells are mammalian, e.g. human, CHO, HEK293T, PER.C6, NS0, myeloma or hybridoma cells.

The invention also relates to monoclonal antibodies that bind to an epitope capable of binding the monoclonal antibody 1F11 or 2F4. The invention also relates to monoclonal antibodies that bind to an epitope capable of binding the monoclonal antibody 5A2. In addition, the invention relates to monoclonal antibodies that bind to an epitope capable of binding the monoclonal antibody 6G4.

Monoclonal and recombinant antibodies are particularly useful in identification and purification of the individual polypeptides or other antigens against which they are directed. The antibodies of the invention have additional utility in that they may be employed as reagents in immunoassays, radioimmunoassays (RIA) or enzyme-linked immunosorbent assays (ELISA). In these applications, the antibodies can be labeled with an analytically-detectable reagent such as a radioisotope, a fluorescent molecule or an enzyme. The antibodies may also be used for the molecular identification and characterization (epitope mapping) of antigens.

Antibodies of the invention can be coupled to a drug for delivery to a treatment site or coupled to a detectable label to facilitate imaging of a site comprising cells of interest, such as cells infected with hCMV. Methods for coupling antibodies to drugs and detectable labels are well known in the art, as are methods for imaging using detectable labels. Labeled antibodies may be employed in a wide variety of assays, employing a wide variety of labels. Detection of the formation of an antibody-antigen complex between an antibody of the invention and an epitope of interest (a hCMV epitope) can be facilitated by attaching a detectable substance to the antibody. Suitable detection means include the use of labels such as radionuclides, enzymes, coenzymes, fluorescers, chemiluminescers, chromogens, enzyme substrates or co-factors, enzyme inhibitors, prosthetic group complexes, free radicals, particles, dyes, and the like. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material is luminol; examples of bioluminescent materials include luciferase, luciferin, and aequorin; and examples of suitable radioactive material include 125I, $^{131}$I, $^{35}$S, or $^3$H. Such labeled reagents may be used in a variety of well-known assays, such as radioimmunoassays, enzyme immunoassays, e.g., ELISA, fluorescent immunoassays, and the like. See for example, references 15-18.

An antibody according to the invention may be conjugated to a therapeutic moiety such as a cytotoxin, a therapeutic agent, or a radioactive metal ion or radioisotope. Examples of radioisotopes include, but are not limited to, I-131, I-123, I-125, Y-90, Re-188, Re-186, At-211, Cu-67, Bi-212, Bi-213, Pd-109, Tc-99, In-111, and the like. Such antibody conjugates can be used for modifying a given biological response; the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin.

Techniques for conjugating such therapeutic moiety to antibodies are well known. See, for example, Arnon et al. (1985) "Monoclonal Antibodies for Immunotargeting of Drugs in Cancer Therapy," in *Monoclonal Antibodies and Cancer Therapy*, ed. Reisfeld et al. (Alan R. Liss, Inc.), pp. 243-256; ed. Hellstrom et al. (1987) "Antibodies for Drug Delivery," in *Controlled Drug Delivery*, ed. Robinson et al. (2d ed; Marcel Dekker, Inc.), pp. 623-653; Thorpe (1985) "Antibody Carriers of Cytotoxic Agents in Cancer Therapy: A Review," in *Monoclonal Antibodies '84: Biological and Clinical Applications*, ed. Pinchera et al. pp. 475-506 (Editrice Kurtis, Milano, Italy, 1985); "Analysis, Results, and Future Prospective of the Therapeutic Use of Radiolabeled Antibody in Cancer Therapy," in *Monoclonal Antibodies for Cancer Detection and Therapy*, ed. Baldwin et al. (Academic Press, New York, 1985), pp. 303-316; and Thorpe et al. (1982) *Immunol. Rev.* 62:119-158.

Alternatively, an antibody can be conjugated to a second antibody to form an antibody heteroconjugate as described in reference 19. In addition, linkers may be used between the labels and the antibodies of the invention [20]. Antibodies or, antigen-binding fragments thereof may be directly labeled with radioactive iodine, indium, yttrium, or other radioactive particle known in the art [21]. Treatment may consist of a combination of treatment with conjugated and nonconjugated antibodies administered simultaneously or subsequently [22, 23].

Antibodies of the invention may also be attached to a solid support.

Additionally, antibodies of the invention or functional antibody fragments thereof, can be chemically modified by covalent conjugation to, for example, a polymer to increase their circulating half-life. Preferred polymers, and methods to attach them to peptides, are shown in references 24-27. Preferred polymers are polyoxyethylated polyols and polyethylene glycol (PEG). PEG is soluble in water at room temperature and has the general formula: $R(O\text{---}CH_2\text{---}CH_2)_nO\text{---}R$ where R can be hydrogen, or a protective group such as an alkyl or alkanol group. Preferably, the protective group has between 1 and 8 carbons, more preferably it is methyl. The symbol n is a positive integer, preferably between 1 and 1,000, more preferably between 2 and 500. The PEG has a preferred average molecular weight between 1,000 and 40,000, more preferably between 2,000 and 20,000, most preferably between 3,000 and 12,000. Preferably, PEG has at least one hydroxy group, more preferably it is a terminal hydroxy group. It is this hydroxy group which is preferably activated to react with a free amino group on the inhibitor. However, it will be understood that the type and amount of the reactive groups may be varied to achieve a covalently conjugated PEG/antibody of the present invention.

Water-soluble polyoxyethylated polyols are also useful in the present invention. They include polyoxyethylated sorbitol, polyoxyethylated glucose, polyoxyethylated glycerol (POG), and the like. POG is preferred. One reason is because the glycerol backbone of polyoxyethylated glycerol is the same backbone occurring naturally in, for example, animals and humans in mono-, di-, triglycerides. Therefore, this branching would not necessarily be seen as a foreign agent in the body. The POG has a preferred molecular weight in the same range as PEG. The structure for POG is shown in reference 28, and a discussion of POG/IL-2 conjugates is found in reference 24.

Another drug delivery system for increasing circulatory half-life is the liposome. Methods of preparing liposome delivery systems are discussed in references 29, 30 and 31. Other drug delivery systems are known in the art and are described in, for example, references 32 and 33.

Antibodies of the invention are preferably provided in purified form. Typically, the antibody will be present in a composition that is substantially free of other polypeptides e.g. where less than 90% (by weight), usually less than 60% and more usually less than 50% of the composition is made up of other polypeptides.

Antibodies of the invention may be immunogenic in non-human (or heterologous) hosts e.g. in mice. In particular, the antibodies may have an idiotope that is immunogenic in non-human hosts, but not in a human host. Antibodies of the invention for human use include those that cannot be obtained from hosts such as mice, goats, rabbits, rats, non-primate mammals, etc. and cannot be obtained by humanisation or from xeno-mice.

Antibodies of the invention can be of any isotype (e.g. IgA, IgG, IgM i.e. an α, γ or μ heavy chain), but will generally be IgG. Within the IgG isotype, antibodies may be IgG1, IgG2, IgG3 or IgG4 subclass. Antibodies of the invention may have a κ or a λ light chain.

Production of Antibodies

Monoclonal antibodies according to the invention can be made by one of the methods known in the art. The general methodology for making monoclonal antibodies using hybridoma technology is well known [34, 35]. Preferably, the alternative EBV immortalization method described in reference 36 is used.

Using the method described in reference 36, B cells producing the antibody of the invention can be transformed with EBV in the presence of a polyclonal B cell activator. Transformation with EBV is a standard technique and can easily be adapted to include polyclonal B cell activators.

Additional stimulants of cellular growth and differentiation may optionally be added during the transformation step to further enhance the efficiency. These stimulants may be cytokines such as IL-2 and IL-15. In a particularly preferred aspect, IL-2 is added during the immortalization step to further improve the efficiency of immortalization, but its use is not essential.

The immortalized B cells produced using these methods can then be cultured using methods known in the art and antibodies isolated therefrom.

Monoclonal antibodies may be further purified, if desired, using filtration, centrifugation and various chromatographic methods such as HPLC or affinity chromatography. Techniques for purification of monoclonal antibodies, including techniques for producing pharmaceutical-grade antibodies, are well known in the art.

Fragments of the monoclonal antibodies of the invention can be obtained from the monoclonal antibodies by methods that include digestion with enzymes, such as pepsin or papain, and/or by cleavage of disulfide bonds by chemical reduction. Alternatively, fragments of the monoclonal antibodies can be obtained by cloning and expression of part of sequences of the heavy or light chains. Antibody "fragments" include Fab, Fab', F(ab')$_2$ and Fv fragments. The invention also encompasses single-chain Fv fragments (scFv) derived from the heavy and light chains of a monoclonal antibody of the invention e.g. the invention includes a scFv comprising the CDRs from an antibody of the invention. Also included are heavy or light chain monomers and dimers as well as single chain antibodies, e.g. single chain Fv in which the heavy and light chain variable domains are joined by a peptide linker.

Standard techniques of molecular biology may be used to prepare DNA sequences coding for the antibodies or fragments of the antibodies of the present invention. Desired DNA sequences may be synthesized completely or in part using oligonucleotide synthesis techniques. Site-directed mutagenesis and polymerase chain reaction (PCR) techniques may be used as appropriate.

Any suitable host cell/vector system may be used for expression of the DNA sequences encoding the antibody molecules of the present invention or fragments thereof. Bacterial, for example *E. coli*, and other microbial systems may be used, in part, for expression of antibody fragments such as Fab and F(ab')$_2$ fragments, and especially Fv fragments and single chain antibody fragments, for example, single chain Fvs. Eukaryotic, e.g. mammalian, host cell expression systems may be used for production of larger antibody molecules, including complete antibody molecules. Suitable mammalian host cells include CHO, HEK293T, PER.C6, NS0, myeloma or hybridoma cells.

The present invention also provides a process for the production of an antibody molecule according to the present invention comprising culturing a host cell comprising a vector of the present invention under conditions suitable for leading to expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

Alternatively, antibodies according to the invention may be produced by i) expressing a nucleic acid sequence according to the invention in a cell, and ii) isolating the expressed antibody product. Additionally, the method may include iii) purifying the antibody.

Screening and Isolation of B Cells

Transformed B cells are screened for those producing antibodies of the desired antigen specificity, and individual B cell clones can then be produced from the positive cells.

The screening step may be carried out by ELISA, by staining of tissues or cells (including transfected cells), a neutralization assay or one of a number of other methods known in the art for identifying desired antigen specificity. The assay may select on the basis of simple antigen recognition, or may select on the additional basis of a desired function e.g. to select neutralizing antibodies rather than just antigen-binding antibodies, to select antibodies that can change characteristics of targeted cells, such as their signaling cascades, their shape, their growth rate, their capability of influencing other cells, their response to the influence by other cells or by other reagents or by a change in conditions, their differentiation status, etc.

The cloning step for separating individual clones from the mixture of positive cells may be carried out using limiting dilution, micromanipulation, single cell deposition by cell sorting or another method known in the art. Preferably the cloning is carried out using limiting dilution.

The immortalized B cell clones of the invention can be used in various ways e.g. as a source of monoclonal antibodies, as a source of nucleic acid (DNA or mRNA) encoding a monoclonal antibody of interest, for research, etc.

The invention provides a composition comprising immortalized B memory lymphocytes, wherein the lymphocytes produce antibodies with high neutralizing potency specific for hCMV, and wherein the antibodies are produced at $\geq 5$ pg per cell per day. The invention also provides a composition comprising clones of an immortalized B memory lymphocyte, wherein the clones produce a monoclonal antibody with a high affinity specific for hCMV, and wherein the antibody is produced at $\geq 5$ pg per cell per day. Preferably said clones produce a monoclonal antibody with a high potency in neutralizing hCMV infection.

Exemplary immortalized B cell clones according to the invention are 1F11, 2F4, 5A2, 9A11 and 6G4.

Further, cell lines expressing exemplary antibodies of the invention, 1F11 and 2F4 were deposited with the Advanced Biotechnology Center (ABC), Largo Rossana Benzi 10, 16132 Genoa (Italy), under the terms of the Budapest Treaty, on Jul. 16, 2008. These deposits are provided for the convenience of those skilled in the art and are neither an admission that such deposits are required to practice the invention nor that equivalent embodiments are not within the skill of the art in view of the present disclosure. The public availability of these deposits is not a grant of a license to make, use or sell the deposited materials under this or any other patents. The nucleic acid sequences of the deposited materials are incorporated in the present disclosure by reference and are controlling if in conflict with any sequence described herein.

Epitopes

As mentioned above, the antibodies of the invention can be used to map the epitopes to which they bind. The inventors have discovered that antibodies 1F11, 2F4, 5A2 and 9A11, that neutralize hCMV infection of endothelial cells, epithelial cells, retinal cells and dendritic cells, are directed towards an epitope determined by a combination of the hCMV proteins UL130 and UL131A. Although the inventors do not wish to be bound to any theory, it is believed that the antibodies 1F11, 2F4, 5A2 and 9A11 bind to either a conformational epitope formed by these two proteins, or bind to one of UL130 and UL131A, the other being required for specificity.

In addition, the inventors have discovered that antibody 6G4 that neutralizes hCMV infection of endothelial cells, epithelial cells, retinal cells, and dendritic cells is directed towards an epitope determined by a combination of hCMV proteins UL128, UL130 and UL131A. Although the inventors do not wish to be bound to any theory, it is believed that the antibody 6G4 binds to either a conformational epitope formed by these three proteins, or binds to one or two of UL128, UL130 and UL131A, the other(s) being required for specificity.

The epitopes recognized by these antibodies may have a number of uses. The epitopes and mimotopes in purified or synthetic form can be used to raise immune responses (i.e. as a vaccine, or for the production of antibodies for other uses) or for screening patient serum for antibodies that immunoreact with the epitopes or mimotopes. Preferably, such an epitope or mimotope, or antigen comprising such an epitope or mimotope is used as a vaccine for raising an immune response. The antibodies of the invention can also be used in a method to monitor the quality of vaccines in particular to check that the antigen in a vaccine contains the correct immunogenic epitope in the correct conformation.

The epitopes may also be useful in screening for ligands that bind to said epitopes. Such ligands preferably block the epitopes and so prevent infection. Such ligands are encompassed within the scope of the invention.

Recombinant Expression

The immortalized memory B cells of the invention may also be used as a source of nucleic acid for the cloning of antibody genes for subsequent recombinant expression. Expression from recombinant sources is more common for pharmaceutical purposes than expression from B cells or hybridomas e.g. for reasons of stability, reproducibility, culture ease, etc.

Thus the invention provides a method for preparing a recombinant cell, comprising the steps of: (i) obtaining one or more nucleic acids (e.g. heavy and/or light chain genes) from the B cell clone that encodes the antibody of interest; and (ii) inserting the nucleic acid into an expression host in order to permit expression of the antibody of interest in that host.

Similarly, the invention provides a method for preparing a recombinant cell, comprising the steps of: (i) sequencing nucleic acid(s) from the B cell clone that encodes the antibody of interest; and (ii) using the sequence information from step (i) to prepare nucleic acid(s) for inserting into an expression host in order to permit expression of the antibody of interest in that host. The nucleic acid may, but need not, be manipulated between steps (i) and (ii) to introduce restriction sites, to change codon usage, and/or to optimize transcription and/or translation regulatory sequences.

The invention also provides a method of preparing a recombinant cell, comprising the step of transforming a host cell with one or more nucleic acids that encode a monoclonal antibody of interest, wherein the nucleic acids are nucleic acids that were derived from an immortalized B cell clone of the invention. Thus the procedures for first preparing the nucleic acid(s) and then using it to transform a host cell can be performed at different times by different people in different places (e.g. in different countries).

These recombinant cells of the invention can then be used for expression and culture purposes. They are particularly useful for expression of antibodies for large-scale pharmaceutical production. They can also be used as the active ingredient of a pharmaceutical composition. Any suitable culture techniques can be used, including but not limited to static culture, roller bottle culture, ascites fluid, hollow-fiber type bioreactor cartridge, modular minifermenter, stirred tank, microcarrier culture, ceramic core perfusion, etc.

Methods for obtaining and sequencing immunoglobulin genes from B cells are well known in the art e.g. see reference 37).

The expression host is preferably a eukaryotic cell, including yeast and animal cells, particularly mammalian cells (e.g. CHO cells, NS0 cells, human cells such as PER.C6 [Crucell;

reference 38] or HKB-11 [Bayer; references 39 & 40] cells, myeloma cells [41 & 42], etc.), as well as plant cells. Preferred expression hosts can glycosylate the antibody of the invention, particularly with carbohydrate structures that are not themselves immunogenic in humans. Expression hosts that can grow in serum-free media are preferred. Expression hosts that can grow in culture without the presence of animal-derived products are preferred.

The expression host may be cultured to give a cell line.

The invention provides a method for preparing one or more nucleic acid molecules (e.g. heavy and light chain genes) that encodes an antibody of interest, comprising the steps of: (i) preparing an immortalized B cell clone according to the invention; (ii) obtaining from the B cell clone nucleic acid that encodes the antibody of interest. The invention also provides a method for obtaining a nucleic acid sequence that encodes an antibody of interest, comprising the steps of: (i) preparing an immortalized B cell clone according to the invention; (ii) sequencing nucleic acid from the B cell clone that encodes the antibody of interest.

The invention also provides a method of preparing nucleic acid molecule(s) that encodes an antibody of interest, comprising the step of obtaining the nucleic acid from a B cell clone that was obtained from a transformed B cell of the invention. Thus the procedures for first obtaining the B cell clone and then preparing nucleic acid(s) from it can be performed at very different times by different people in different places (e.g. in different countries).

The invention provides a method for preparing an antibody (e.g. for pharmaceutical use), comprising the steps of: (i) obtaining and/or sequencing one or more nucleic acids (e.g. heavy and light chain genes) from the selected B cell clone expressing the antibody of interest; (ii) inserting the nucleic acid(s) into or using the nucleic acid(s) to prepare an expression host that can express the antibody of interest; (iii) culturing or sub-culturing the expression host under conditions where the antibody of interest is expressed; and, optionally, (iv) purifying the antibody of the interest.

The invention also provides a method of preparing an antibody comprising the steps of: culturing or sub-culturing an expression host cell population under conditions where the antibody of interest is expressed and, optionally, purifying the antibody of the interest, wherein said expression host cell population has been prepared by (i) providing nucleic acid(s) encoding a selected B cell the antibody of interest that is produced by a population of B memory lymphocytes prepared as described above, (ii) inserting the nucleic acid(s) into an expression host that can express the antibody of interest, and (iii) culturing or sub-culturing expression hosts comprising said inserted nucleic acids to produce said expression host cell population. Thus the procedures for first preparing the recombinant expression host and then culturing it to express antibody can be performed at very different times by different people in different places (e.g. in different countries).

Pharmaceutical Compositions

The use of antibodies as the active ingredient of pharmaceuticals is now widespread, including the products Herceptin™ (trastuzumab), Rituxan™, Campath™, Remicade™, ReoPro™, Mylotarg™, Zevalin™, Omalizumab, Synagis™ (Palivizumab), Zenapax™ (daclizumab), etc.

The invention thus provides a pharmaceutical composition containing the antibodies of the invention and/or nucleic acid encoding such antibodies and/or immortalized B cells that express such antibodies and/or the epitopes recognized by the antibodies of the invention. A pharmaceutical composition may also contain a pharmaceutically acceptable carrier to allow administration. The carrier should not itself induce the production of antibodies harmful to the individual receiving the composition and should not be toxic. Suitable carriers may be large, slowly metabolized macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Preferred forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilizing and/or dispersing agents. Alternatively, the antibody molecule may be in dry form, for reconstitution before use with an appropriate sterile liquid.

Once formulated, the compositions of the invention can be administered directly to the subject. It is preferred that the compositions are adapted for administration to human subjects.

The pharmaceutical compositions of this invention may be administered by any number of routes including, but not limited to, oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule. Known antibody-based pharmaceuticals provide guidance relating to frequency of administration e.g. whether a pharmaceutical should be delivered daily, weekly, monthly, etc. Frequency and dosage may also depend on the severity of symptoms.

Compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition, like Synagis™ and Herceptin™, for reconstitution with sterile water containing a preservative). The composition may be prepared for topical administration e.g. as an ointment, cream or powder. The composition may be prepared for oral administration e.g. as a tablet or capsule, as a spray, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops. The composition may be in kit form, designed such that a combined composition is reconstituted just prior to administration to a patient. For example, a lyophilized antibody can be provided in kit form with sterile water or a sterile buffer.

It will be appreciated that the active ingredient in the composition will be an antibody molecule, an antibody fragment or variants and derivatives thereof. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Gennaro (2000) *Remington: The Science and Practice of Pharmacy*, 20th edition, ISBN: 0683306472. Pharmaceutical compositions of the invention generally have a pH between 5.5 and 8.5, preferably between 6 and 8, and more preferably about 7. The pH may be maintained by the use of a buffer. The composition may be sterile and/or pyrogen free. The composition may be isotonic with respect to humans. Pharmaceutical compositions of the invention are preferably supplied in hermetically-sealed containers.

Pharmaceutical compositions will include an effective amount of one or more antibodies of the invention and/or one or more immortalized B cells of the invention and/or a polypeptide comprising an epitope that binds an antibody of the invention i.e. an amount that is sufficient to treat, ameliorate, or prevent a desired disease or condition, or to exhibit a detectable therapeutic effect. Therapeutic effects also include reduction in physical symptoms. The precise effective amount for any particular subject will depend upon their size and health, the nature and extent of the condition, and the therapeutics or combination of therapeutics selected for administration. The effective amount for a given situation is determined by routine experimentation and is within the judgment of a clinician. For purposes of the present invention, an effective dose will generally be from about 0.01 mg/kg to about 50 mg/kg, or about 0.05 mg/kg to about 10 mg/kg of the compositions of the present invention in the individual to which it is administered. Known antibody-based pharmaceuticals provide guidance in this respect e.g. Herceptin™ is administered by intravenous infusion of a 21 mg/ml solution, with an initial loading dose of 4 mg/kg body weight and a weekly maintenance dose of 2 mg/kg body weight; Rituxan™ is administered weekly at 375 mg/m$^2$; etc.

Compositions can include more than one (e.g. 2, 3, 4, 5, etc.) antibody of the invention, particularly where such antibodies bind to different antigens (or to different epitopes in the same antigen) to provide an additive or synergistic therapeutic effect. For example, one antibody may bind to a combination of the hCMV proteins UL130 and UL131A (or complex) while another may bind to gB. In a further example, one antibody may bind to the combination of UL128, UL130 and UL131A while another may bind to epitopes in the hCMV proteins gB, gH, gL, gM, gN, gO, UL128, UL130, UL131A and combinations thereof. Thus, one antibody may be targeted to the mechanism that mediates infection of fibroblasts, while the other antibody may be targeted to the mechanism that mediates infection of endothelial cells. For optimal clinical effect it may well be advantageous to address both mechanisms of hCMV infection and maintenance.

Antibodies of the invention may be administered (either combined or separately) with other therapeutics e.g. with chemotherapeutic compounds, with radiotherapy, etc. Preferred therapeutic compounds include anti-viral compounds such as ganciclovir, foscarnet and cidofovir. Such combination therapy provides an additive or synergistic improvement in therapeutic efficacy relative to the individual therapeutic agents when administered alone. The term "synergy" is used to describe a combined effect of two or more active agents that is greater than the sum of the individual effects of each respective active agent. Thus, where the combined effect of two or more agents results in "synergistic inhibition" of an activity or process, it is intended that the inhibition of the activity or process is greater than the sum of the inhibitory effects of each respective active agent. The term "synergistic therapeutic effect" refers to a therapeutic effect observed with a combination of two or more therapies wherein the therapeutic effect (as measured by any of a number of parameters) is greater than the sum of the individual therapeutic effects observed with the respective individual therapies.

Antibodies may be administered to those patients who have previously shown no response to treatment for hCMV infection, i.e. have been shown to be refractive to anti-hCMV treatment. Such treatment may include previous treatment with an anti-viral agent. This may be due to, for example, infection with an anti-viral resistant strain of hCMV.

In compositions of the invention that include antibodies of the invention, the antibodies preferably make up at least 50% by weight (e.g. 60%, 70%, 80%, 90%, 95%, 97%, 98%, 99% or more) of the total protein in the composition. The antibodies are thus in purified form.

The invention provides a method of preparing a pharmaceutical, comprising the steps of: (i) preparing an antibody of the invention; and (ii) admixing the purified antibody with one or more pharmaceutically-acceptable carriers.

The invention also provides a method of preparing a pharmaceutical, comprising the step of admixing an antibody with one or more pharmaceutically-acceptable carriers, wherein the antibody is a monoclonal antibody that was obtained from a transformed B cell of the invention. Thus the procedures for first obtaining the monoclonal antibody and then preparing the pharmaceutical can be performed at very different times by different people in different places (e.g. in different countries).

As an alternative to delivering antibodies or B cells for therapeutic purposes, it is possible to deliver nucleic acid (typically DNA) to a subject that encodes the monoclonal antibody (or active fragment thereof) of interest, such that the nucleic acid can be expressed in the subject in situ to provide a desired therapeutic effect. Suitable gene therapy and nucleic acid delivery vectors are known in the art.

Compositions of the invention may be immunogenic compositions, and are more preferably vaccine compositions comprising an antigen comprising an epitope found on a combination of the hCMV proteins UL130 and UL131A. Alternative compositions may comprise (i) an antigen comprising an epitope found on a combination of the hCMV proteins UL130 and UL131A, and (ii) an antigen comprising an epitope found on the hCMV proteins gH, gB or a combination of gM and gN. In another embodiment, compositions of the invention may be immunogenic compositions, and may be vaccine compositions comprising an antigen comprising an epitope found on a combination of hCMV proteins UL128, UL130 and UL131A. Alternative compositions may comprise (i) an antigen comprising an epitope formed by a combination of the hCMV proteins UL128, UL130 and UL131A, and (ii) an antigen comprising an epitope found on the hCMV proteins gB, gH or a combination of gM and gN. Vaccines according to the invention may either be prophylactic (i.e. to prevent infection) or therapeutic (i.e. to treat infection), but will typically be prophylactic.

Compositions may include an antimicrobial, particularly if packaged in a multiple dose format.

Compositions may comprise detergent e.g. a Tween (polysorbate), such as Tween 80. Detergents are generally present at low levels e.g. <0.01%.

Compositions may include sodium salts (e.g. sodium chloride) to give tonicity. A concentration of 10±2 mg/ml NaCl is typical.

Compositions may comprise a sugar alcohol (e.g. mannitol) or a disaccharide (e.g. sucrose or trehalose) e.g. at around 15-30 mg/ml (e.g. 25 mg/ml), particularly if they are to be lyophilised or if they include material which has been reconstituted from lyophilized material. The pH of a composition for lyophilisation may be adjusted to around 6.1 prior to lyophilization.

The compositions of the invention may also comprise one or more immunoregulatory agents. Preferably, one or more of the immunoregulatory agents include(s) an adjuvant.

The epitope compositions of the invention will preferably elicit both a cell mediated immune response as well as a humoral immune response in order to effectively address a hCMV infection. This immune response will preferably induce long lasting (e.g. neutralizing) antibodies and a cell mediated immunity that can quickly respond upon exposure to hCMV.

Medical Treatments and Uses

The antibodies, antibody derivative of the invention or antibody fragments thereof may be used for the treatment of hCMV infection, for the prevention of hCMV infection or for the diagnosis of hCMV infection.

Methods of diagnosis may include contacting an antibody or an antibody fragment with a sample. Such samples may be tissue samples taken from, for example, salivary glands, lung, liver, pancreas, kidney, ear, eye, placenta, alimentary tract, heart, ovaries, pituitary, adrenals, thyroid, brain or skin. The methods of diagnosis may also include the detection of an antigen/antibody complex.

The invention therefore provides (i) an antibody, an antibody fragment, or variants and derivatives thereof according to the invention, (ii) an immortalized B cell clone according to the invention, (iii) an epitope capable of binding one of 1F11 or 2F4, or 6G4 or (iv) an epitope capable of binding one of 5A2 or 9A11, for use in therapy or (v) a ligand, preferably an antibody, capable of binding an epitope that binds an antibody of the invention, e.g., 1F11, 2F4 or 6G4, for use in therapy.

Also provided is a method of treating a patient comprising administering to that patient (i) an antibody according to the invention, (ii) an epitope capable of binding one of 1F11 or 2F4, or 6G4 or (iii) an epitope capable of binding one of 5A2 or 9A11, or (iv) a ligand, preferably an antibody, capable of binding an epitope capable of binding one of 1F11, 2F4 or 6G4.

The invention also provides the use of (i) an antibody, an antibody fragment, or variants and derivatives thereof according to the invention, (ii) an immortalized B cell clone according to the invention, (iii) an epitope capable of binding one of 1F11 or 2F4, or 6G4, (iv) a ligand, preferably an antibody, that binds to an epitope capable of binding one of 1F11 or 2F4 or 6G4, (v) an epitope capable of binding one of 5A2 or 9A11, or 6G4, or (vi) a ligand, preferably an antibody, that binds to an epitope capable of binding one of 5A2 or 9A11, or 6G4 in the manufacture of a medicament for the prevention or treatment of hCMV infection.

The invention provides a composition of the invention for use as a medicament. It also provides the use of an antibody of the invention and/or a protein comprising an epitope to which such an antibody binds in the manufacture of a medicament for treatment of a patient and/or diagnosis in a patient. It also provides a method for treating a subject and/or of performing diagnosis on a subject, comprising the step of administering to them a composition of the invention. The subject is preferably a human. One way of checking efficacy of therapeutic treatment involves monitoring disease symptoms after administration of the composition of the invention. Treatment can be a single dose schedule or a multiple dose schedule. The invention is useful for the treatment of hCMV infection.

Preferably, an antibody, immortalized B cell clone, epitope or composition according to the invention is administered to groups of subjects particularly at risk of or susceptible to hCMV infection. Such subjects groups include immunocompromised subjects, such as those suffering from HIV or undergoing immunosuppressive therapy, such as transplant patients.

Antibodies of the invention can be used in passive immunization.

Antibodies and fragments thereof as described in the present invention may also be used in a kit for the diagnosis of hCMV infection.

Epitopes capable of binding an antibody of the invention, e.g., the monoclonal antibody 1F11 or 2F4 or 6G4 may be used in a kit for monitoring the efficacy of vaccination procedures by detecting the presence of protective anti-hCMV antibodies.

Epitopes capable of binding an antibody of the invention e.g., the monoclonal antibody 5A2 or 9A11 described in the present invention may be used in a kit for monitoring the efficacy of vaccination procedures by detecting the presence of protective anti-hCMV antibodies.

Antibodies, antibody fragments or variants or derivatives thereof as described in the present invention may also be used in a kit for monitoring vaccine manufacture with the desired immunogenicity.

The invention also provides a method of preparing a pharmaceutical, comprising the step of admixing a monoclonal antibody with one or more pharmaceutically-acceptable carriers, wherein the monoclonal antibody is a monoclonal antibody that was obtained from an expression host of the invention. Thus the procedures for first obtaining the monoclonal antibody (e.g. expressing it and/or purifying it) and then admixing it with the pharmaceutical carrier(s) can be performed at very different times by different people in different places (e.g. in different countries).

Starting with a transformed B cell of the invention, various steps of culturing, sub-culturing, cloning, sub-cloning, sequencing, nucleic acid preparation etc. can be performed in order to perpetuate the antibody expressed by the transformed B cell, with optional optimization at each step. In a preferred embodiment, the above methods further comprise techniques of optimization (e.g. affinity maturation or optimization) applied to the nucleic acids encoding the antibody. The invention encompasses all cells, nucleic acids, vectors, sequences, antibodies etc. used and prepared during such steps.

In all these methods, the nucleic acid used in the expression host may be manipulated to insert, delete or amend certain nucleic acid sequences. Changes from such manipulation include, but are not limited to, changes to introduce restriction sites, to amend codon usage, to add or optimize transcription and/or translation regulatory sequences, etc. It is also possible to change the nucleic acid to alter the encoded amino acids. For example, it may be useful to introduce one or more (e.g.

1, 2, 3, 4, 5, 6, 7, 8, 9, 10, etc.) amino acid substitutions, one or more (e.g. 1, 2, 3, 4, 5, 6, 7, 8, 9, 10, etc.) amino acid deletions and/or one or more (e.g. 1, 2, 3, 4, 5, 6, 7, 8, 9, 10, etc.) amino acid insertions into the antibody's amino acid sequence. Such point mutations can modify effector functions, antigen-binding affinity, post-translational modifications, immunogenicity, etc., can introduce amino acids for the attachment of covalent groups (e.g. labels) or can introduce tags (e.g. for purification purposes). Mutations can be introduced in specific sites or can be introduced at random, followed by selection (e.g. molecular evolution). For instance, one or more nucleic acids encoding any of the CDR regions, heavy chain variable regions or light chain variable regions of antibodies of the invention can be randomly or directionally mutated to introduce different properties in the encoded amino acids. Such changes can be the result of an iterative process wherein initial changes are retained and new changes at other nucleotide positions are introduced. Moreover, changes achieved in independent steps may be combined. Different properties introduced into the encoded amino acids may include, but are not limited to, enhanced affinity, General The term "comprising" encompasses "including" as well as "consisting of" e.g. a composition "comprising" X may consist exclusively of X or may include something additional e.g. X+Y.

The word "substantially" does not exclude "completely" e.g. a composition which is "substantially free" from Y may be completely free from Y.

The term "about" in relation to a numerical value x means, for example, x±10%.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

As used herein, reference to "treatment" of a patient is intended to include prevention and prophylaxis. The term "patient" means all mammals including humans. Examples of patients include humans, cows, dogs, cats, horses, goats, sheep, pigs, and rabbits. Preferably, the patient is a human.

The following are methods which can be used to practice the invention.

EXAMPLES

Example 1

Cloning of B Cells and Screening for hCMV Neutralizing Activity

Two donors with high hCMV neutralizing antibody titers in the serum were identified. Memory B cells were isolated and immortalized using EBV and CpG as described in reference 36. Briefly, memory B cells were isolated by negative selection using CD22 beads, followed by removal of IgM+, IgD+ IgA+ B cells using specific antibodies and cell sorting. The sorted cells (IgG+) were immortalized with EBV in the presence of CpG 2006 and irradiated allogeneic mononuclear cells. Replicate cultures each containing 50 memory B cells were set up in twenty 96 well U bottom plates. After two weeks the culture supernatants were collected and tested for their capacity to neutralize hCMV infection of either endothelial cells, epithelial cells or fibroblasts in separate assays. B cell clones were isolated from positive polyclonal cultures as described in reference 36. IgG concentrations in the supernatant of selected clones were determined using an IgG-specific ELISA.

For the viral neutralization assay a titrated amount of a clinical hCMV isolate was mixed with an equal volume of culture supernatant or with dilutions of human sera containing neutralizing antibodies. After 1 hour incubation at room temperature the mixture was added to confluent monolayers of either endothelial cells (e.g. HUVEC cells or HMEC-1 cells), epithelial cells or fibroblasts in 96 well flat bottom plates and incubated at 37° C. for two days. The supernatant was discarded, the cells were fixed with cold methanol and stained with a mixture of mouse monoclonal antibodies to hCMV early antigens, followed by a fluorescein-labeled goat anti mouse Ig. The plates were analyzed using a fluorescence microscope. In the absence of neutralizing antibodies the infected cells were ~1,000/field, while in the presence of saturating concentrations of neutralizing antibodies the infection was completely inhibited. The neutralizing titer is indicated as the concentration of antibody (μg/ml) that gives a 50% reduction of hCMV infection.

Table 3 shows that three different types of antibodies have been identified. Those that can neutralize infection of fibroblasts, those that can neutralize infection of endothelial cells and those that can neutralize infection of both. This agrees with previous data that different proteins are responsible for tropism towards a particular cell type [7]. In addition to neutralization of endothelial cells, 1F11 and 2F4 were observed to neutralize infection of epithelial cells, retinal cells and dendritic cells (data not shown).

TABLE 3

| | | 50% neutralization (μg/ml) | |
|---|---|---|---|
| Clone | Specificity | Fibroblasts | Endothelial cells |
| 1F11 | UL130/UL131A | * | 0.001 |
| 2F4 | UL130/UL131A | * | 0.003 |
| 5A2 | UL130/UL131A | * | 0.002 |
| 9A11 | UL130/UL131A | * | 0.001 |
| 7H3 | gB | 2 | * |
| 10C6 | gB | 0.3 | 0.3 |
| 5F1 | gB | 0.3 | 0.3 |
| 6B4 | gB | 0.5 | 2 |
| Cytotec^ | | 5000 | 50 |
| Donor's Serum | | 33 | 1 |

* no neutralisation at the highest concentration tested (i.e. >2 μg/ml).
^Cytotect (Biotest) is a pool of hCMV hyperimmune IgG.

Some antibodies neutralized infection of both fibroblasts and endothelial cells at IgG concentrations ranging from 0.3 to 0.5 μg/ml. Other antibodies (1F11, 5A2, 9A11 and 2F4) failed to neutralize hCMV infection of fibroblasts, but neutralized the infection of endothelial cells and did so at extremely low concentrations ranging from 0.001 to 0.004 μg/ml (more than 1,000 fold more potent than previously known antibodies capable of neutralizing infection of non-fibroblast cells).

Note that since the initial characterization, it has been determined that 5F1 binds to an epitope of gB rather than gH. This is consistent with the results which demonstrate that blocking gB allows neutralization of infection of fibroblasts as observed for 7H3, 10C6 and 6B4.

Table 4 shows that 6G4, which has been shown to be specific for a combination of the hCMV proteins UL128, UL130 and UL131A, was able to neutralize hCMV infection of endothelial cells, retinal cells and dendritic cells at very low concentrations (i.e. with high potency).

TABLE 4

| | | 50% neutralisation (µg/ml) | |
|---|---|---|---|
| Clone | Specificity | Fibroblasts | Endothelial/retinal/dendritic cells |
| 6G4 | UL128/UL130/UL131A | * | 0.004 |
| Cytotec^ | | 5000 | 50 |
| Donor's Serum | | 33 | 1 |

\* no neutralisation at the highest concentration tested (i.e. >2 µg/ml).

^Cytotect (Biotest) is a pool of hCMV hyperimmune IgG.

Example 2

Identification of the Target Antigens Recognized by the Monoclonal Antibodies Human MRC-9 fibroblasts were infected with a clinical hCMV isolate. After 3 days the cells were metabolically labeled with $^{35}$S Methionine and Cysteine. After preclearance of the lysate human monoclonal antibodies 1F11 and 2F4 were added and immunocomplexes were precipitated by the addition of Protein A beads and resolved on SDS-PAGE (FIG. 1). A human monoclonal IgG antibody with irrelevant specificity was used as negative control. The results show that human monoclonal antibodies 1F11 and 2F4 precipitate complexes of hCMV proteins.

Figure 2:
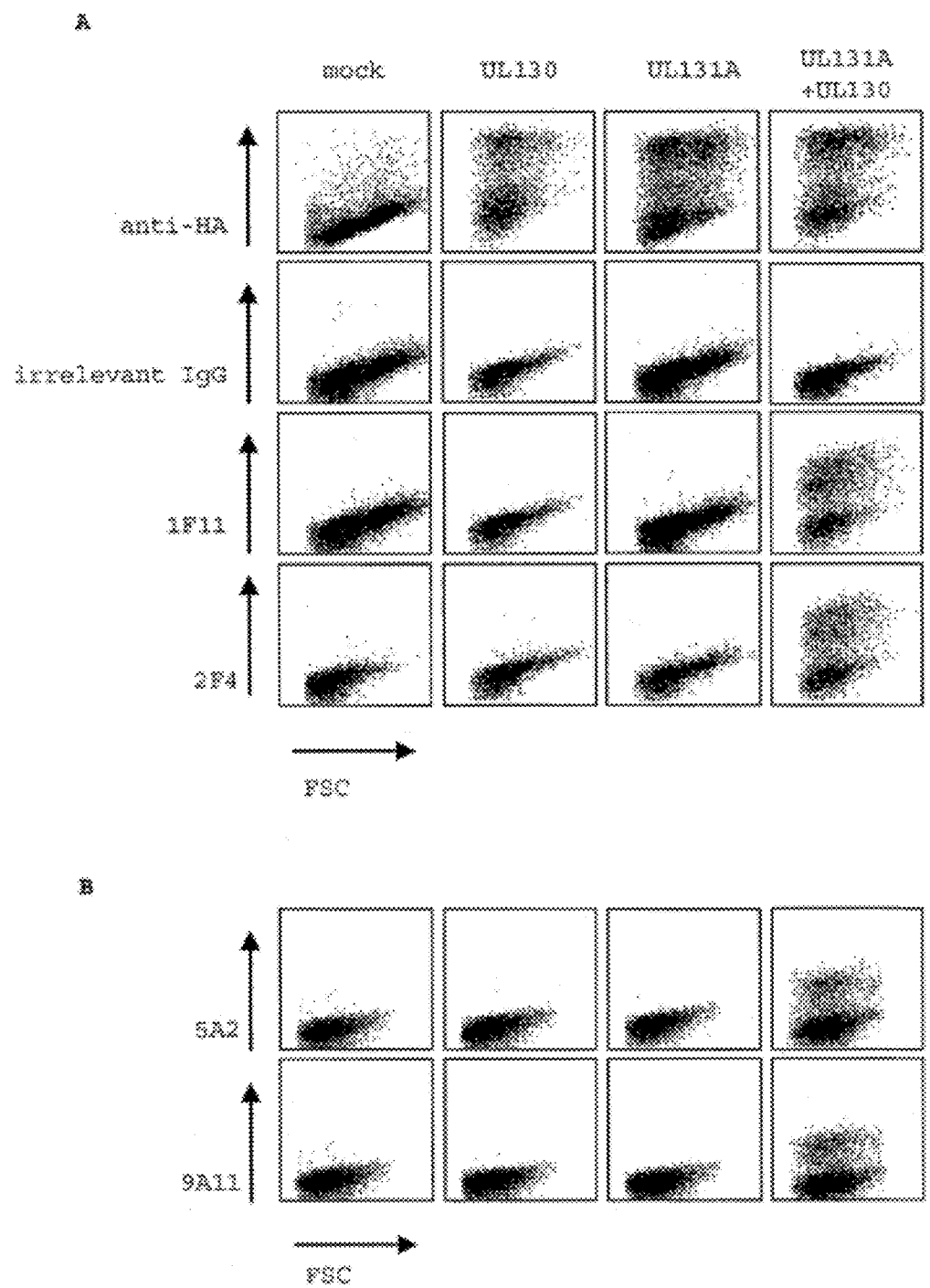
FIG. 2 shows a FACS analysis which demonstrates that human monoclonal antibodies (A) 1F11 and 2F4 and (B) 5A2 and 9A11 recognize an epitope determined by a combination of the hCMV proteins UL130 and UL131A.
Figure 6:
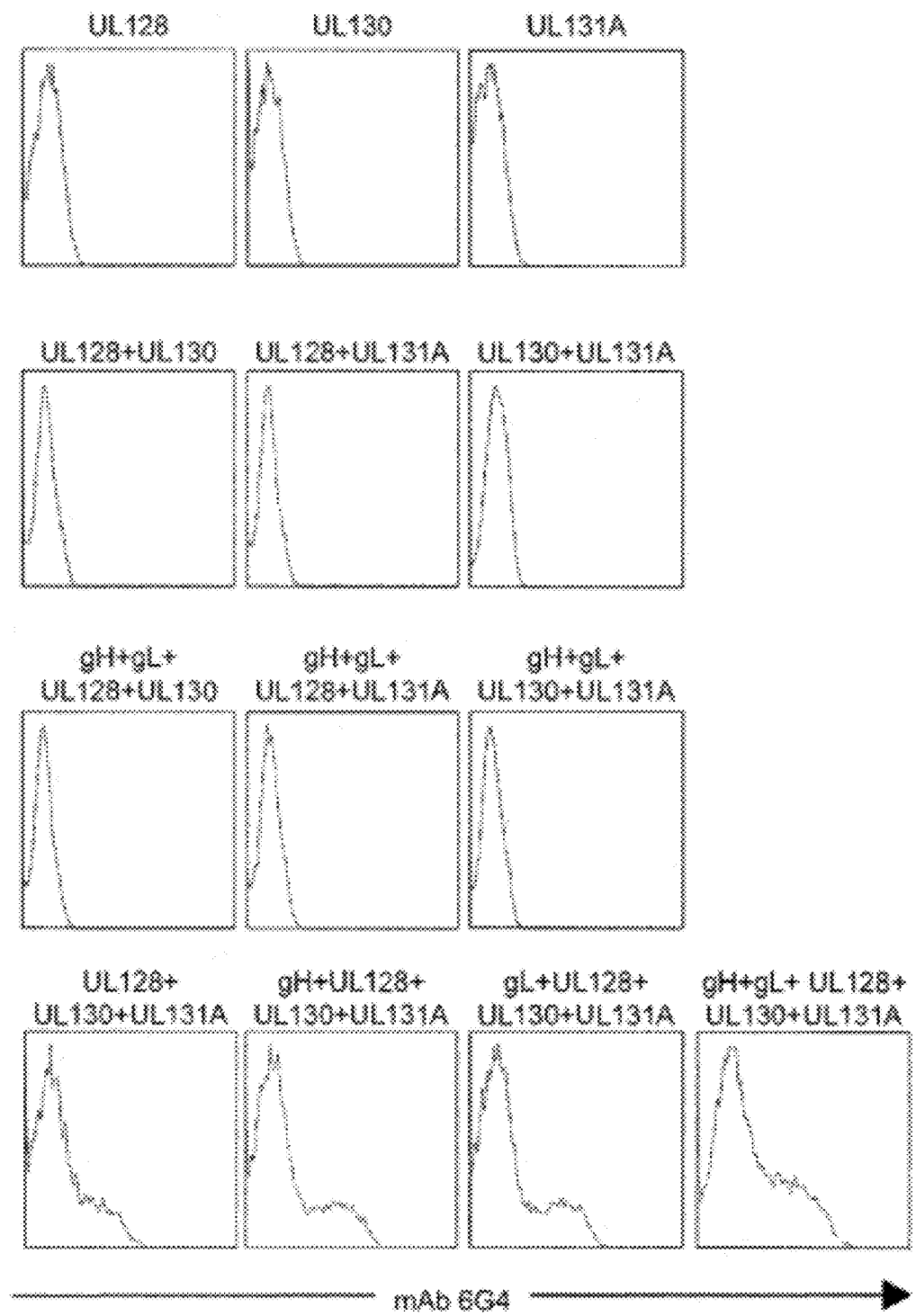
FIG. 6 shows FACS analysis which demonstrates that the human monoclonal antibody 6G4 recognizes an epitope determined by the hCMV proteins UL128, UL130 and UL131A.

To map the specificity of the human monoclonal antibodies, expression vectors encoding hemagglutinin (HA)-tagged UL128Δ1-27, UL130Δ1-25 and UL131AΔ1-18 hCMV proteins lacking signal peptides were constructed. Vectors encoding full length hCMV proteins UL128, UL130, UL131A, gH, and gL were constructed as well. HEK293T cells were transfected with these vectors alone or in combination. After 36 h, cells were fixed, permeabilized and stained with an anti-HA antibody (to control for efficiency of transfection) and with monoclonal antibodies followed by a goat anti-human IgG. A HuMab IgG with irrelevant specificity was used as negative control. FIG. 2A shows that the human monoclonal antibodies 1F11 and 2F4 recognize an epitope determined by a combination of the hCMV proteins UL130 and UL131A. FIG. 2B shows that the human monoclonal antibodies 5A2 and 9A11 recognize an epitope determined by a combination of the hCMV proteins UL130 and UL131A. Antibody 6G4 stained cells co-expressing at least full length UL128, UL130 and UL131A. The intensity of the 6G4 staining was increased when gH and gL were co-transfected together with UL128, UL130 and UL131A to reconstitute the putative whole glycoprotein complex gCIII (FIG. 6). These data suggest that the monoclonal antibody 6G4 is specific for an epitope determined by a combination of the hCMV proteins UL128, UL130 and UL131A (FIG. 6). Most likely this epitope is in the proper conformation only when UL128, UL130 and UL131A are assembled in gCIII with gH and gL.

It will be understood that the invention has been described by way of example only and modifications may be made whilst remaining within the scope and spirit of the invention.

CONCLUSIONS

The above results define human monoclonal antibodies that are capable of neutralizing with high potency and selectivity hCMV infection of human endothelial cells and epithelial cells. To identify the epitope recognized, the antibodies were tested for their capacity to immunoprecipitate proteins from hCMV infected cells (FIG. 1). Human monoclonal antibodies 1F11 and 2F4 precipitated several proteins with apparent molecular weights of ~15, 33-35 and ~100 KDa. These patterns are compatible with the precipitation of a complex containing gH, gL and UL128, UL130 and possibly UL131A.

To better define the target of these antibodies we characterized their capacity to stain HEK293T cells transfected with vectors encoding HA-tagged UL128, UL130 and UL131A. As shown in FIG. 2A, 1F11 and 2F4 stained only cells coexpressing UL130 and UL131A, suggesting that they recognize a conformational epitope determined by a combination of these two hCMV proteins. This conclusion is supported by the fact that these antibodies do not react in a western blot with lysates of infected or transfected cells run under reducing, denaturing, conditions (data not shown).

Similar results were observed for 5A2 and 9A11. FIG. 2b shows that these antibodies stained only cells coexpressing UL130 and UL131A, suggesting that they recognize a conformational epitope determined by a combination of these two hCMV proteins. In addition, as shown in FIG. 6, antibody 6G4 appears to be specific for a conformational epitope determined by a combination of the hCMV proteins UL128, UL130 and UL131A.

Example 3

Figure 4:
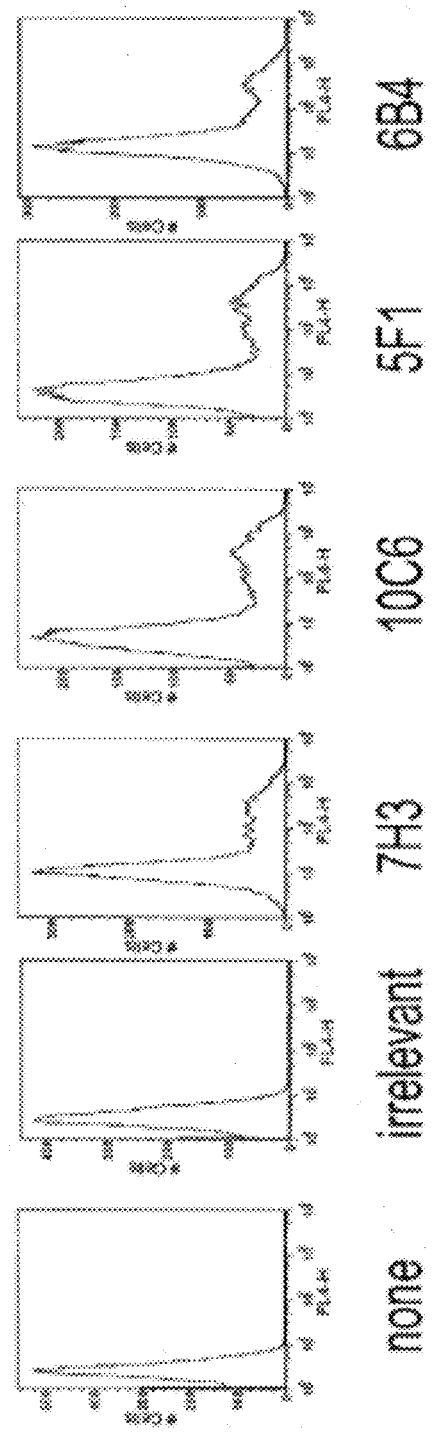
FIG. 4 shows a FACS analysis which demonstrates that the human monoclonal antibodies 7H3, 10C6, 5F1 and 6B4 recognize an epitope on hCMV protein gB.

Further Identification of the Target Antigens Recognized by the Monoclonal Antibodies To map specificities of human monoclonal antibodies neutralizing infection of fibroblasts an expression vector encoding full length gB was constructed. HEK293T cells were transfected with this vector. After 36 h, cells were fixed, permeabilized and stained with human monoclonal antibodies (HuMab) followed by goat anti-human IgG. FIG. 4 shows that monoclonal antibodies 7H3, 10C6, 5F1, and 6B4 (but not an IgG antibody of an irrelevant specificity) specifically stained cells transfected with gB, indicating that they recognize an epitope of gB. Of note, the monoclonal antibodies 10C6, 5F1 and 6B4 neutralize infection of fibroblasts and endothelial cells, whereas the monoclonal antibody 7H3 neutralizes the infection of fibroblasts (but not of endothelial cells). This notion suggests that the monoclonal antibodies 10C6, 5F1, and 6B4 bind to a functional epitope of gB that is distinct from the epitope bound by the monoclonal antibody 7H3.

It will be understood that the invention has been described by way of example only and modifications may be made whilst remaining within the scope and spirit of the invention.

REFERENCES

The Contents of which are Hereby Incorporated by Reference

[1] Plachter, B., C. Sinzger, and G. Jahn. 1996. Cell types involved in replication and distribution of human cytomegalovirus. *Adv Virus Res* 46:195-261.

[2] Gerna, G., E. Percivalle, F. Baldanti, and M. G. Revello. 2002. Lack of transmission to polymorphonuclear leukocytes and human umbilical vein endothelial cells as a marker of attenuation of human cytomegalovirus. *J Med Virol* 66:335-339.

[3] Adler, B., L. Scrivano, Z. Ruzcics, B. Rupp, C. Sinzger, and U. Koszinowski. 2006. Role of human cytomegalovirus UL131A in cell type-specific virus entry and release. *J Gen Virol* 87:2451-2460.

[4] Gerna, G., E. Percivalle, D. Lilleri, L. Lozza, C. Fornara, G. Hahn, F. Baldanti, and M. G. Revello. 2005. Dendritic-cell infection by human cytomegalovirus is restricted to strains carrying functional UL131-128 genes and mediates efficient viral antigen presentation to CD8+ T cells. *J Gen Virol* 86:275-284.

[5] Hahn, G., M. G. Revello, M. Patrone, E. Percivalle, G. Campanini, A. Sarasini, M. Wagner, A. Gallina, G. Milanesi, U. Koszinowski, F. Baldanti, and G. Gerna. 2004. Human cytomegalovirus UL131-128 genes are indispensable for virus growth in endothelial cells and virus transfer to leukocytes. *J Virol* 78:10023-10033.

[6] Patrone, M., M. Secchi, L. Fiorina, M. Ierardi, G. Milanesi, and A. Gallina. 2005. Human cytomegalovirus UL130 protein promotes endothelial cell infection through a producer cell modification of the virion. *J Virol* 79:8361-8373.

[7] Wang, D., and T. Shenk. 2005. Human cytomegalovirus virion protein complex required for epithelial and endothelial cell tropism. *Proc Natl Acad Sci USA* 102:18153-18158.

[8] Wang, D., and T. Shenk. 2005. Human cytomegalovirus UL131 open reading frame is required for epithelial cell tropism. *J Virol* 79:10330-10338.

[9] Nigro, G., S. P. Adler, R. La Torre, and A. M. Best. 2005. Passive immunization during pregnancy for congenital cytomegalovirus infection. *N Engl J Med* 353:1350-1362.

[10] Borucki et al. (2004) *Antiviral Res* 64:103-111.

[11] McLean et al. (2005) *J Immunol,* 174:4768-4778.

[12] Lefranc, M P. et al. 2003 IMGT unique numbering for immunoglobulin and T cell receptor variable domains and Ig superfamily V-like domains. *Dev Comp Immunol.* 27(1): 55-77.

[13] Lefranc, M P. 1997. Unique database numbering system for immunogenetic analysis. *Immunology Today,* 18:509.

[14] Lefranc, M P. 1999. The IMGT unique numbering for Immunoglobulins, T cell receptors and Ig-like domains. *The Immunologist,* 7:132-136.

[15] U.S. Pat. No. 3,766,162
[16] U.S. Pat. No. 3,791,932
[17] U.S. Pat. No. 3,817,837
[18] U.S. Pat. No. 4,233,402
[19] U.S. Pat. No. 4,676,980
[20] U.S. Pat. No. 4,831,175
[21] U.S. Pat. No. 5,595,721
[22] WO00/52031
[23] WO00/52473
[24] U.S. Pat. No. 4,766,106
[25] U.S. Pat. No. 4,179,337
[26] U.S. Pat. No. 4,495,285
[27] U.S. Pat. No. 4,609,546
[28] Knauf et al. (1988) *J. Bio. Chem.* 263:15064-15070
[29] Gabizon et al. (1982) *Cancer Research* 42:4734
[30] Cafiso (1981) *Biochem Biophys Acta* 649:129
[31] Szoka (1980) *Ann. Rev. Biophys. Eng.* 9:467
[32] Poznansky et al. (1980) *Drug Delivery Systems* (R. L. Juliano, ed., Oxford, N.Y.) pp. 253-315
[33] Poznansky (1984) *Pharm Revs* 36:277
[34] Kohler, G. and Milstein, C, 1975, *Nature* 256:495-497.
[35] Kozbar et al. 1983, *Immunology Today* 4:72.
[36] WO2004/076677
[37] Chapter 4 of *Kuby Immunology* (4th edition, 2000; ASIN: 0716733315
[38] Jones et al. *Biotechnol Prog* 2003, 19(1):163-8
[39] Cho et al. *Cytotechnology* 2001,37:23-30
[40] Cho et al. *Biotechnol Prog* 2003,19:229-32
[41] U.S. Pat. No. 5,807,715
[42] U.S. Pat. No. 6,300,104

The invention claimed is:

1. A method of inhibiting human cytomegalovirus (hCMV) infection in a subject, comprising administering an effective amount of an antibody, or antigen binding portion thereof, comprising heavy and light chain variable region CDR1, CDR2, and CDR3 sequences as set forth in SEQ ID NO: 51, SEQ ID NO: 52, SEQ ID NO: 53, and SEQ ID NO: 54, SEQ ID NO: 55, SEQ ID NO: 56, respectively, wherein hCMV infection is inhibited.

2. A method of inhibiting hCMV infection in a subject, comprising administering an effective amount of an antibody, or antigen binding portion thereof, comprising heavy and light chain variable regions comprising the amino acid sequence of SEQ ID NO: 63 and SEQ ID NO: 64, respectively, wherein hCMV infection is inhibited.

3. A method of inhibiting hCMV infection in a subject, comprising administering an effective amount of an antibody, or antigen binding portion thereof, that binds to the same epitope as an antibody having heavy and a light chain variable regions comprising the amino acid sequence of SEQ ID NO: 63 and SEQ ID NO: 64, respectively, wherein hCMV infection is inhibited.

4. The method of claim 1, 2, or 3 wherein the antibody is a human antibody, a monoclonal antibody, a human monoclonal antibody, a single chain antibody, Fab, Fab', $F(ab')_2$, Fv or scFv.

5. The method of claim 1, 2, or 3 further comprising the administration of a second antibody, or antigen binding fragment thereof, which inhibits hCMV infection.

6. The method of claim 5, wherein the second antibody, or antigen binding fragment thereof, is specific for the hCMV protein gB.

7. The method of claim 1, 2, or 3 wherein the antibody is specific for a complex comprising hCMV proteins UL128, UL130 and UL131A and inhibits infection of endothelial cells, retinal cells, or dendritic cells by hCMV, wherein the concentration of antibody required for 50% inhibition of hCMV is 0.1 µg/ml or less.

8. The method of claim 7, wherein the concentration of antibody required for 50% inhibition of hCMV is 0.01 µg/ml or less.

9. The method of claim 7, wherein the concentration of antibody required for 50% inhibition of hCMV is 0.004 µg/ml or less.

10. The method of claim 7, wherein the antibody binds a conformational epitope formed by the three proteins.

* * * * *